United States Patent
Kelly et al.

[11] Patent Number: 6,089,861
[45] Date of Patent: Jul. 18, 2000

[54] CARRIER FOR SUPPORTING ORTHODONTIC APPLIANCES

[75] Inventors: John S. Kelly, Arcadia; Russell A. Jordan, Rancho Cucamonga; James D. Cleary, Glendora; Evangelos G. Georgakis, Alta Loma; Robert C. Manemann, Huntington Beach, all of Calif.

[73] Assignee: 3M Innovative Properties Company, St. Paul, Minn.

[21] Appl. No.: 09/178,660

[22] Filed: Oct. 26, 1998

Related U.S. Application Data

[63] Continuation-in-part of application No. 08/947,095, Oct. 8, 1997, Pat. No. 5,827,058.

[51] Int. Cl.⁷ .................................................. A61C 3/00
[52] U.S. Cl. .............................. 433/9; 433/17; 206/63.5; 206/368
[58] Field of Search .................. 433/8, 9, 17; 206/63.5, 206/368, 369, 460, 461, 813

[56] References Cited

U.S. PATENT DOCUMENTS

| | | | |
|---|---|---|---|
| 3,250,003 | 5/1966 | Collito | 32/14 |
| 3,361,252 | 1/1968 | Wise | 206/56 |
| 3,378,925 | 4/1968 | Faller | 32/71 |
| 3,698,547 | 10/1972 | Roberts et al. | 206/57 |
| 3,709,866 | 1/1973 | Waller | 260/27 |
| 3,745,653 | 7/1973 | Cohl | 32/14 |
| 3,854,581 | 12/1974 | Jones, Jr. | 206/460 |
| 4,055,249 | 10/1977 | Kojima | 206/447 |
| 4,204,325 | 5/1980 | Kaelble | 433/9 |
| 4,701,129 | 10/1987 | Hazard | 433/136 |
| 4,801,528 | 1/1989 | Bennett | 433/220 |
| 4,817,805 | 4/1989 | Rodriguez | 211/71 |
| 4,859,184 | 8/1989 | Hazard | 433/136 |
| 4,903,840 | 2/1990 | So | 206/581 |
| 4,948,367 | 8/1990 | Haas | 433/9 |
| 4,952,204 | 8/1990 | Korteweg | 604/1 |
| 4,978,007 | 12/1990 | Jacobs et al. | 206/469 |
| 4,979,611 | 12/1990 | Bolliger et al. | 206/83 |
| 5,015,180 | 5/1991 | Randklev | 433/9 |
| 5,172,809 | 12/1992 | Jacobs et al. | 206/368 |
| 5,172,810 | 12/1992 | Brewer | 206/369 |
| 5,183,403 | 2/1993 | Masuhara et al. | 433/9 |
| 5,221,202 | 6/1993 | James | 433/9 |
| 5,279,800 | 1/1994 | Berry, Jr. | 422/300 |
| 5,328,363 | 7/1994 | Chester et al. | 433/9 |
| 5,348,154 | 9/1994 | Jacobs et al. | 206/369 |
| 5,368,161 | 11/1994 | Plais | 206/369 |
| 5,429,229 | 7/1995 | Chester et al. | 206/63.5 |
| 5,484,283 | 1/1996 | Franetzki | 433/116 |
| 5,538,129 | 7/1996 | Chester et al. | 206/63.5 |
| 5,542,844 | 8/1996 | Perret, Jr. | 433/9 |
| 5,552,177 | 9/1996 | Jacobs et al. | 427/2.29 |
| 5,575,645 | 11/1996 | Jacobs et al. | 433/9 |
| 5,636,736 | 6/1997 | Jacobs et al. | 306/369 |
| 5,653,588 | 8/1997 | Moschik | 433/8 |

FOREIGN PATENT DOCUMENTS

| | | |
|---|---|---|
| 452 492 A1 | 10/1991 | European Pat. Off. . |
| PCT/JP89/ 01109 | 5/1991 | WIPO . |
| WO 92/08419 | 5/1992 | WIPO ............... A61C 7/12 |

*Primary Examiner*—Nicholas D. Lucchesi
*Attorney, Agent, or Firm*—James D. Christoff

[57] ABSTRACT

An orthodontic assembly includes one or more orthodontic appliances that are releasably received in a carrier. The carrier has arms with outer end sections that are spaced apart from each other to present a channel therebetween. The outer end sections of the arms are received in recesses of each appliance in order to support the appliance in suspended relation. The carrier is particularly useful for holding appliances during a manufacturing operation or during transport of the appliances from manufacturing operation to another. The carrier is also useful for supporting appliances in a package for shipment to the end user, especially when the appliances are precoated with a layer of adhesive.

38 Claims, 23 Drawing Sheets

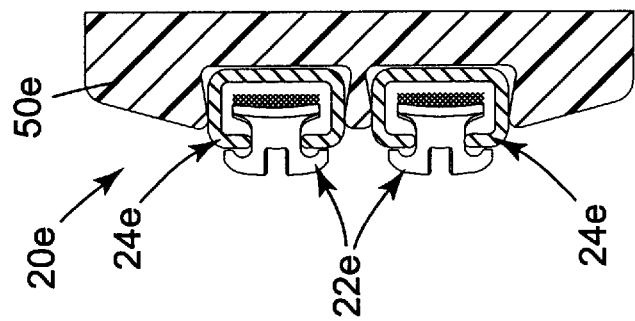
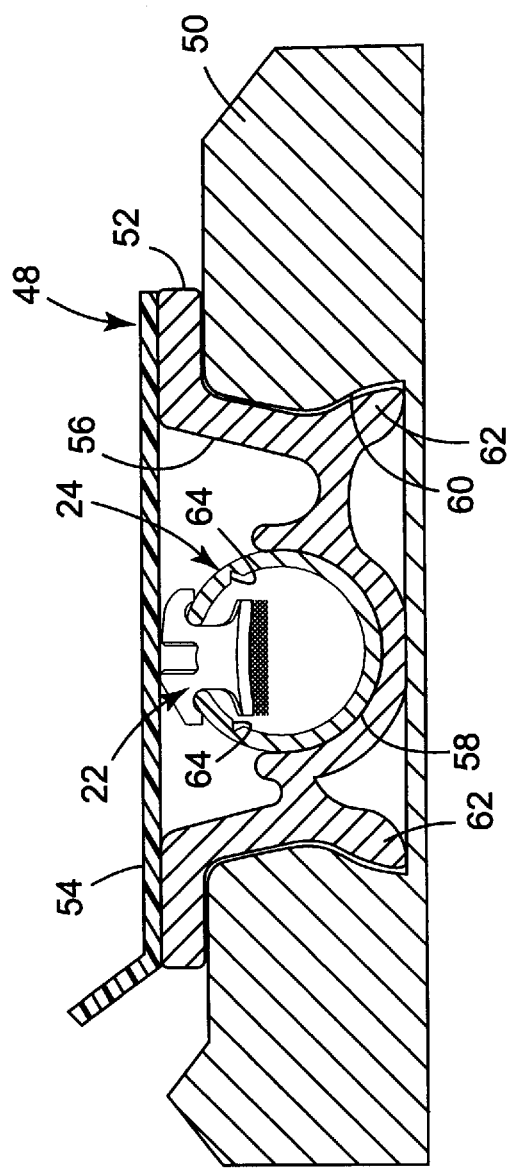

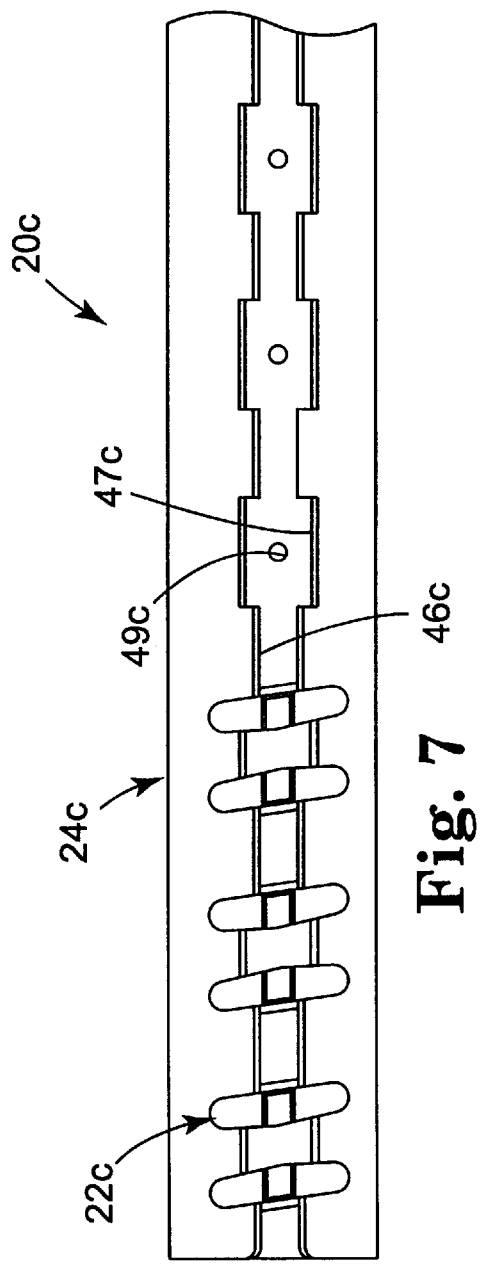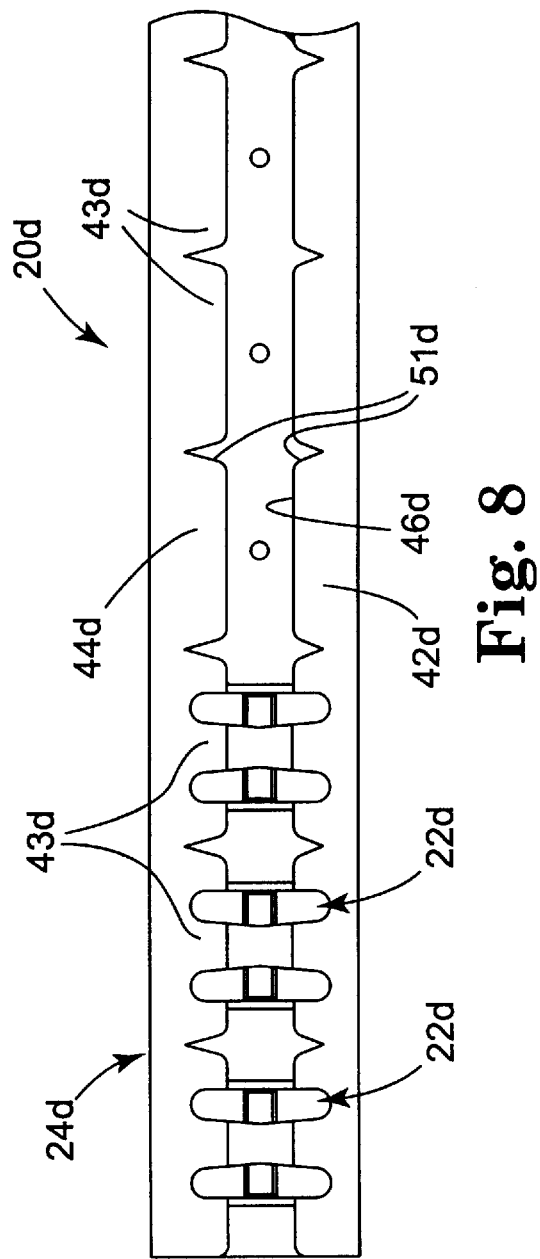

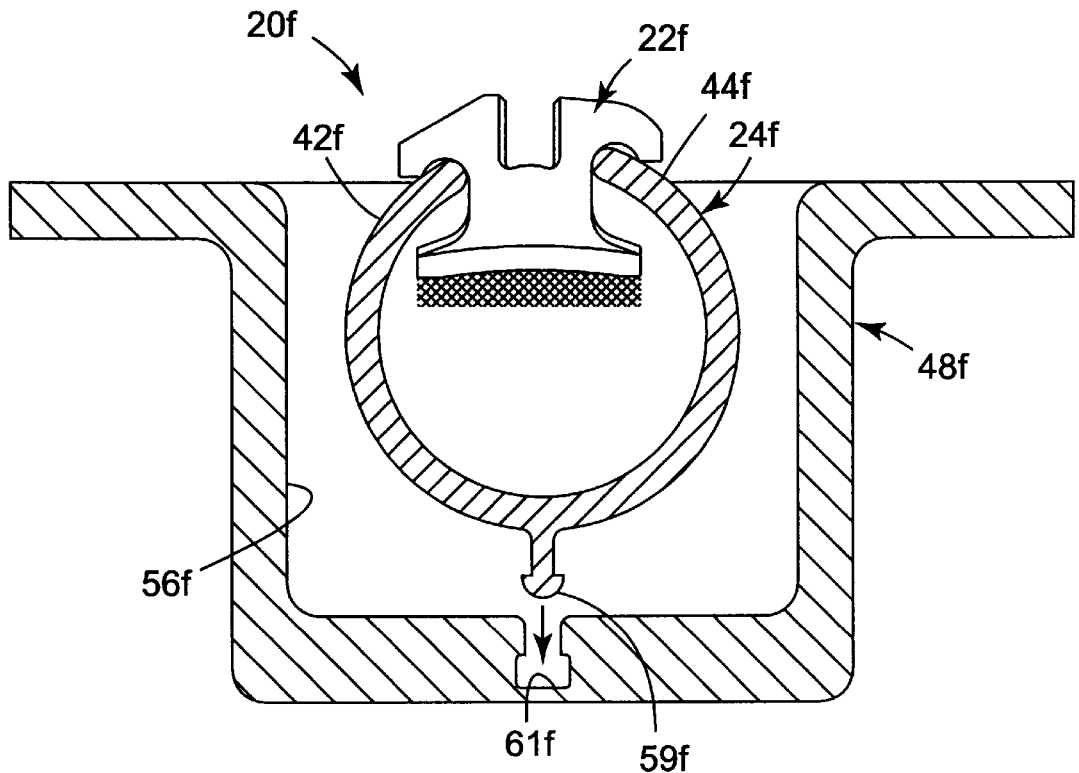
Fig. 11
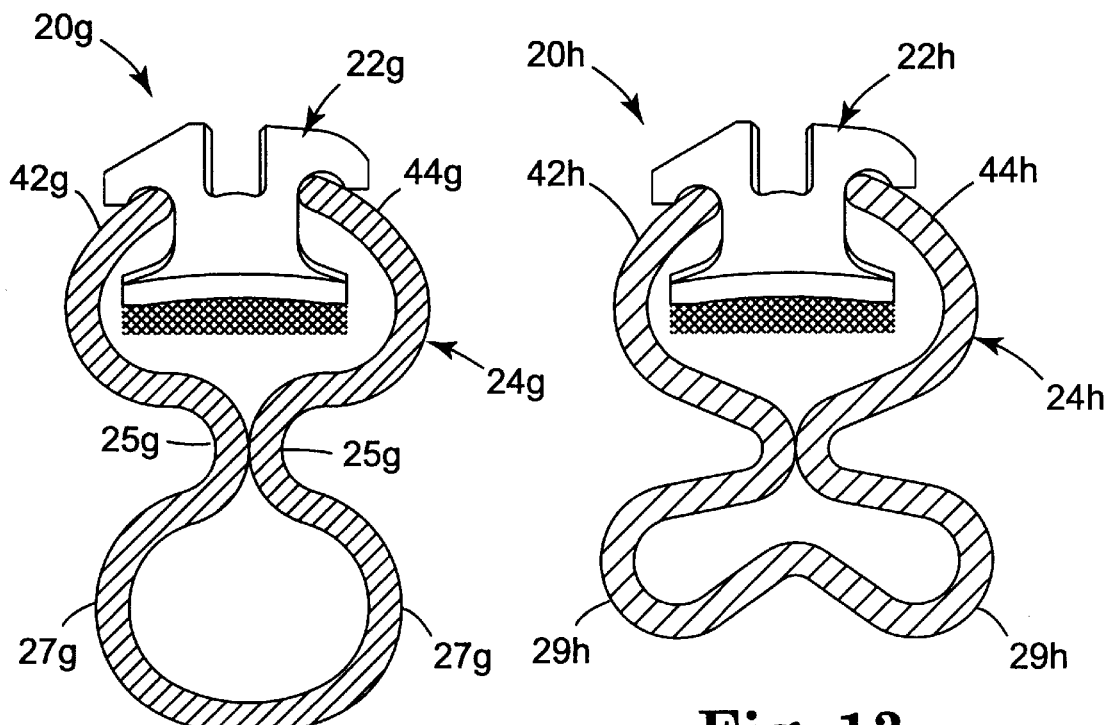
Fig. 12
Fig. 13

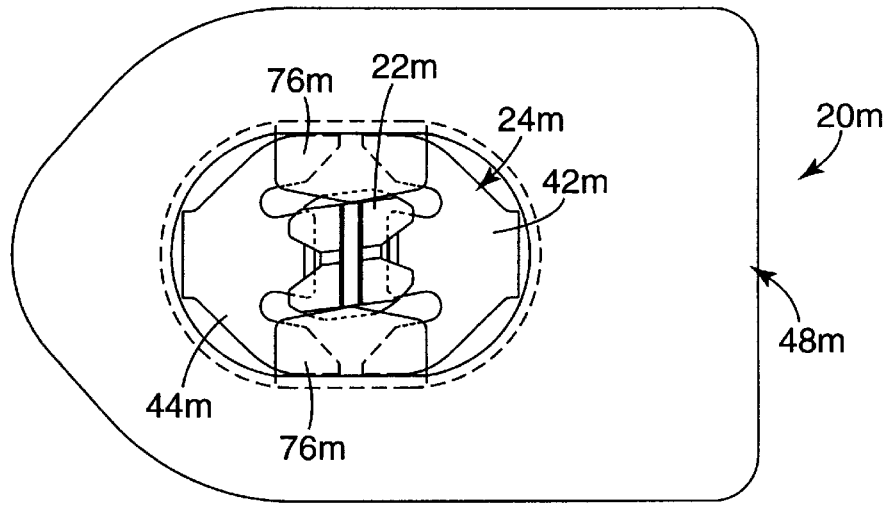
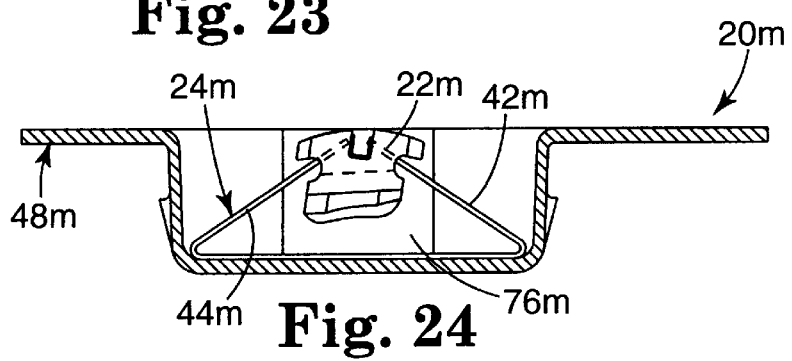
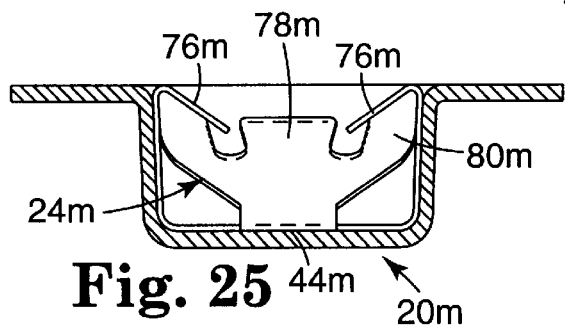
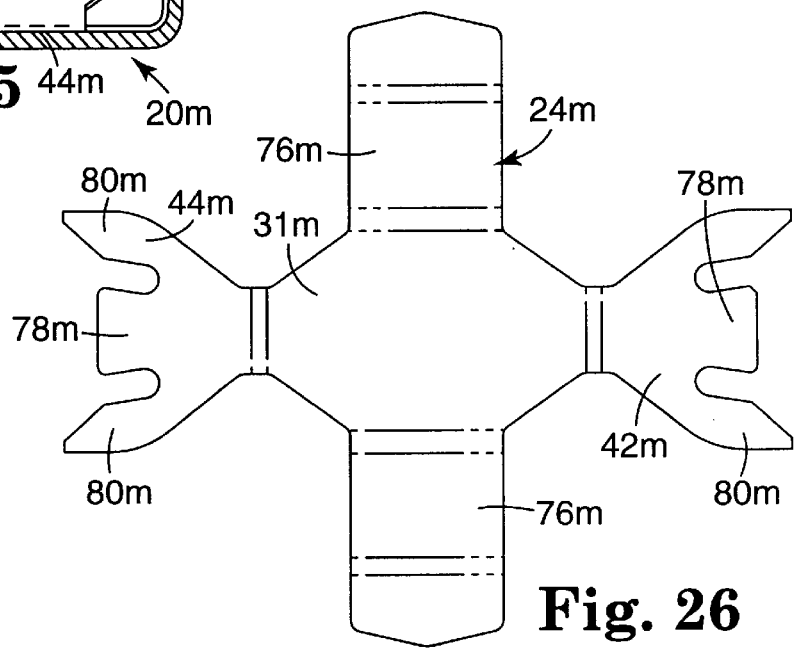
Fig. 23
Fig. 24
Fig. 25
Fig. 26

CARRIER FOR SUPPORTING ORTHODONTIC APPLIANCES

This is a continuation-in-part of application Ser. No. 08/947,095 filed Oct. 8, 1997, now U.S. Pat. No. 5,827,058.

BACKGROUND OF THE INVENTION

1. Field of the Invention

This invention relates to a carrier for supporting orthodontic appliances such as brackets and buccal tubes of the type used in orthodontic treatment. The carrier is particularly useful for supporting the appliances during their manufacture, during the time that the appliances are received within a container for shipment to an end user and also during the time that the brackets are arranged in a set-up tray in a dental operatory in preparation for application to a patient's tooth surface.

2. Description of the Related Art

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth.

In the past, orthodontic appliances were connected to teeth by welding or brazing each bracket or buccal tube to a band that was then placed over the desired tooth in encircling relation. In more recent years, however, it has become common practice to bond orthodontic appliances directly to the surface of the tooth. Orthodontic brackets that are directly bonded to tooth surfaces provide a more aesthetic appearance than the appearance of brackets that are welded to bands, and help alleviate the problem of a "tinsel tooth" or "metallic mouth" appearance that is often associated with orthodontic treatment.

For many years, it was common practice to apply orthodontic adhesive to the base of directly-bonded appliances immediately before the appliances were placed on the tooth. In some instances, a quantity of adhesive was dispensed onto a mixing pad or dispensing well and a small spatula or other hand instrument was then used to apply a small dab of adhesive to each appliance. In other instances, a quantity of adhesive was dispensed from a syringe directly onto the base of the appliance.

Adhesive precoated brackets are also now available and represent a significant advantage to the orthodontist. Adhesive precoated brackets have a bonding base upon which the manufacturer has applied a precise quantity of adhesive such as a photocurable adhesive. When it is desired to mount the bracket on a tooth, the bracket is simply removed from the package and is placed directly onto the tooth surface.

Examples of adhesive precoated brackets are described in U.S. Pat. Nos. 4,978,007, 5,015,180 and 5,328,363, all of which are assigned to the assignee of the present invention. In certain embodiments of the inventions described in those patents, the bracket and adhesive are packaged in a container that protects the adhesive from light, evaporation, oxidation, contamination, humidity and sublimation. In some of those embodiments, the coating of adhesive on the packaged bracket is in contact with a release liner or coating that helps prevent the adhesive from being disturbed when the bracket is lifted from the package for use.

As can be appreciated, adhesive precoated brackets represent a significant time savings for the orthodontic practitioner because the adhesive need not be carefully applied to the base of each bracket before placement of the bracket onto the patient's tooth. In addition, the manufacturer can control the quantity of adhesive placed on the bracket so that there is sufficient adhesive to substantially fill the space between the bracket base and the tooth when the bracket is pushed into position, and yet there is not an inordinate amount of adhesive that might otherwise require excessive clean-up around the perimeter of the bracket base. Optionally, the adhesive is a light-curable adhesive so that the bracket can be carefully positioned in a proper orientation on the tooth surface before a curing lamp is activated to cure the adhesive and securely fix the bracket in place.

In general, the adhesives used for adhesive precoated brackets that are contained in a package having a release liner or coating are more viscous (i.e. less fluid) than other available orthodontic bonding adhesives, in part to ensure that the adhesive retains its shape and does not separate or distort when the bracket is lifted from the package for use. However, some orthodontists prefer the use of less viscous (i.e. more fluid) adhesives in order to facilitate manipulation of the bracket before the adhesive is cured. For example, brackets with less viscous adhesives are relatively easy to slide along the tooth surface when an effort is made align the bracket in a proper, precise orientation on the tooth before the adhesive is cured.

Some practitioners prefer two component chemical-cure adhesives (such as Unite brand adhesive, from 3M Unitek Corporation) to light-curable adhesives. It has been proposed in the past to package orthodontic brackets with one component of a chemical-cure adhesive on each bracket base, and then apply the second component to each bracket base and/or to the patient's tooth once the bracket is removed from the package. Presently, there is a need in the art for an improved package suitable for both chemical-cure adhesives as well as light-curable adhesives.

Moreover, there is increased interest in optimizing the manufacture of orthodontic brackets. Manufacturing optimization may include, for example, automation of the processes for handling of the brackets from the time of manufacture to the time of packaging, as well as increased efficiency of applying the adhesive to the base of the brackets in instances where the brackets are sold with a coating of adhesive. Such improvements in manufacturing can not only reduce costs and processing time, but also may result in a decrease of problems that might otherwise attributed to human error.

SUMMARY OF THE INVENTION

The present invention is directed toward a method and apparatus for supporting orthodontic appliances during manufacture and/or also while the appliances are received in a shipping container or placed in a set-up tray in the dental operatory. The invention involves the use of a carrier having arms that extend toward each other and engage the appliance in respective recesses of the appliance.

In more detail, the present invention is directed in one aspect to an assembly that includes an orthodontic bracket and a carrier. The orthodontic bracket has a base, a body extending from the base and at least two opposed tiewings extending away from the body. The base and at least one of the tiewings extends past the body in a gingival direction and presents a gingival recess. The base and at least one other of the tiewings extends past the body in an occlusal direction and presents an occlusal recess. The carrier has a pair of arms extending toward each other. Each of the arms has an outer end section, and the outer end sections are spaced apart from each other and present a channel therebetween. The bracket is located in the channel and is supported by the arms with one of the outer end sections extending into the occlusal recess and the other of the outer end sections extending into the gingival recess.

The present invention is also directed toward an assembly that comprises an orthodontic buccal tube having a base, a body extending from the base, a mesial side and a distal side. The buccal tube includes a mesial recess adjacent said mesial side and a distal recess adjacent said distal side. The assembly also includes a carrier having a pair of arms extending toward each other. Each of the arms has an outer end section supporting the buccal tube. The outer end section of one of the arms is located in the mesial recess, and the outer end section of the other arm is located in the distal recess.

In another aspect, the invention concerns a method of supporting orthodontic brackets and comprises the step of providing a carrier having a pair of arms extending toward each other, wherein each arm includes an outer end section and wherein the outer end sections are spaced apart from each other and present a channel therebetween. The method also includes the step of moving a bracket along the channel until the bracket is located between the outer end sections, with one of the outer end sections received in an occlusal recess of the bracket and the other outer end section received in a gingival recess of the bracket.

These and other aspects of the invention are described in the text that follows as well as in the accompanying drawings.

BRIEF DESCRIPTION OF THE DRAWINGS

FIG. 4 is a side cross-sectional view of one bracket and the carrier illustrated in FIGS. 1 and 2, wherein the carrier is mounted in a container and the container has been received in a chair-side holder for use in the dental operatory;

FIG. 7 is a fragmentary plan view of a carrier according to another embodiment of the present invention;

FIG. 8 is a plan view of a carrier according to yet another embodiment of the invention;

FIG. 10 is a side cross-sectional view of the carriers, the bracket and the tray illustrated in FIG. 9;

FIG. 11 is a side cross-sectional view of a carrier and container according to an additional embodiment of the invention;

FIG. 12 is a side cross-sectional view of an assembly that includes a bracket and a carrier according to another embodiment of the invention;

FIG. 13 is a view somewhat similar to FIG. 12 except in accordance with still another embodiment of the invention;

FIG. 23 is a plan view of an assembly that is somewhat similar to FIG. 16 except in accordance with still another embodiment of the invention;

FIG. 24 is a side cross-sectional view of the assembly shown in FIG. 23;

FIG. 25 is an end cross-sectional view of the assembly shown in FIGS. 23 and 24;

FIG. 26 is a view of a carrier of the assembly shown in FIGS. 23–25 as the carrier appears before it is placed in a container of the assembly;

DETAILED DESCRIPTION OF THE PREFERRED EMBODIMENTS

Figure 1:
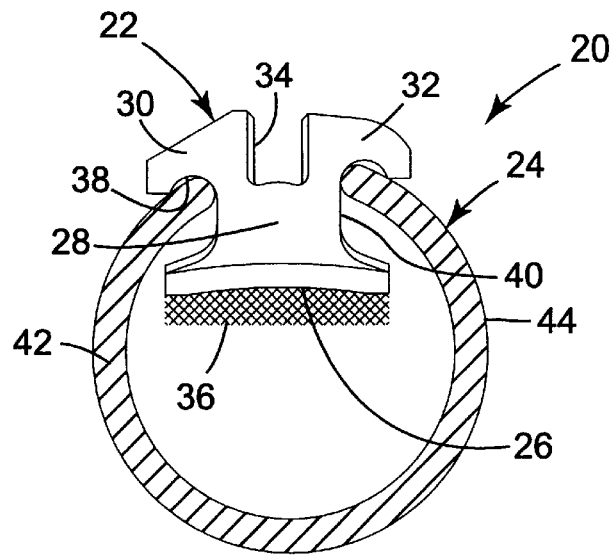
FIG. 1 is side cross-sectional view of an assembly that includes an orthodontic bracket and a carrier for the bracket according to one embodiment of the invention.
Figure 2:
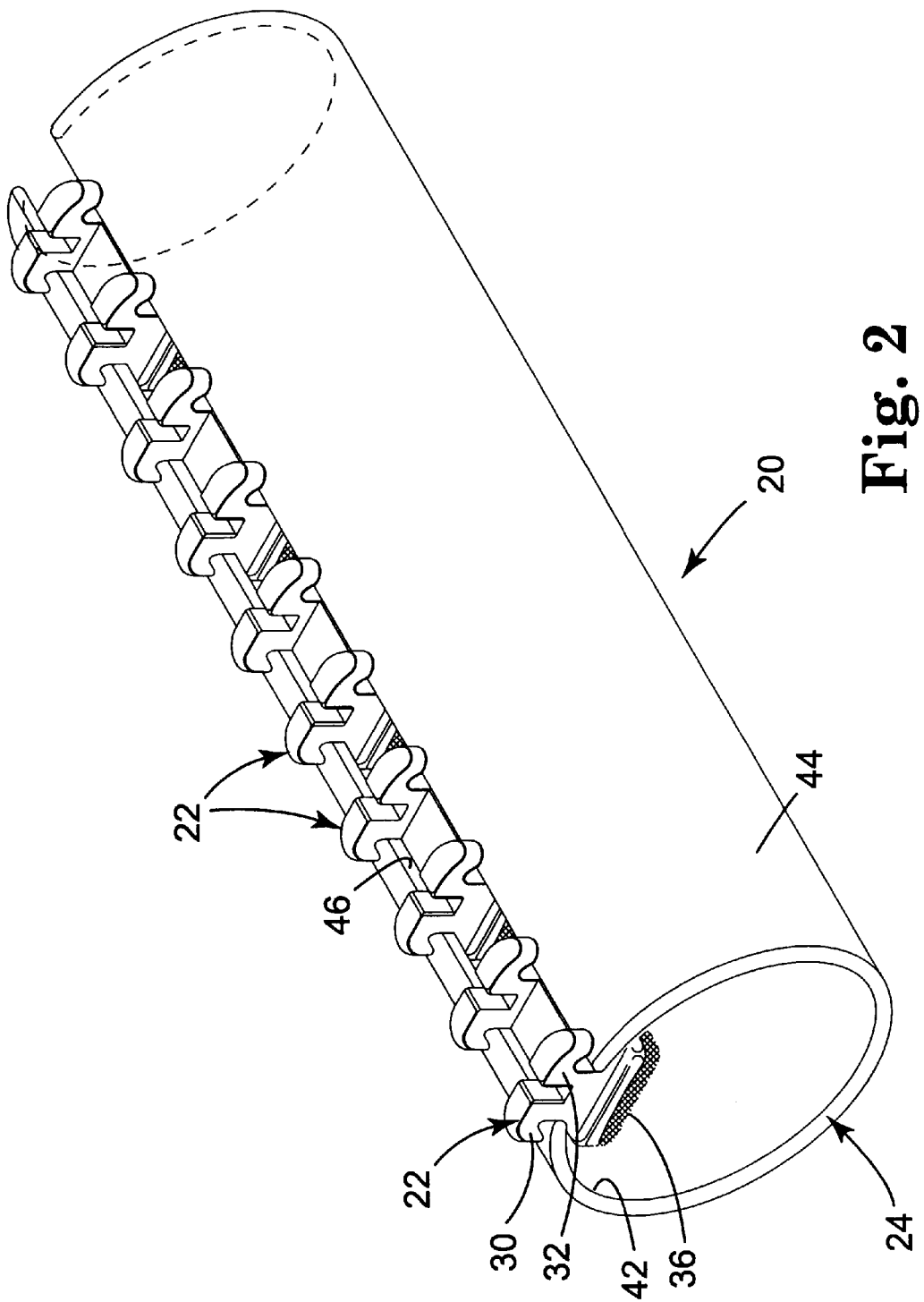
FIG. 2 is a perspective view of the assembly shown in FIG. 1, and illustrating an additional quantity of brackets supported by the carrier.

An orthodontic assembly according to one embodiment of the invention is shown in FIGS. 1 and 2 and is broadly designated by the numeral 20. The assembly 20 includes an orthodontic appliance such as a bracket 22 as well as a carrier 24 for releasably supporting the bracket 22.

The bracket 22 has a tooth-facing base 26 with a compound concave contour that is adapted to match the convex contour of the tooth for which it is intended. A body 28 extends outwardly from the base 26 and at least two tiewings extend away from the body 28. The bracket 22 that is shown in FIGS. 1 and 2 for exemplary purposes is a "twin tiewing" bracket having a pair of spaced apart gingival tiewings 30 that are connected to one side of the body 28 and a pair of spaced apart occlusal tiewings 32 that are connected to an opposite side of the body 28. However, it should be understood in this regard that a "single tiewing" bracket having a single gingival tiewing and a single occlusal tiewing may be used with the assembly 20 as an alternative to the bracket 22 illustrated in the drawings.

Furthermore, the bracket 22 may have a configuration other than that shown in the drawings. For example, the bracket 22 may be angulated and/or be constructed with torque in accordance with selected treatment techniques. The bracket 22 may also be made of any one of a variety of materials, including metal (such as stainless steel), plastic (such as polycarbonate) or ceramic (such as monocrystalline or polycrystalline alumina). If made of plastic or ceramic, the bracket 22 is preferably translucent such that the color of the patient's tooth is visible through the bracket.

An archwire slot 34 is located between the pair of gingival tiewings 30 and the pair of occlusal tiewings 32, and is defined on its lingual side by a labial surface of the body 28. Preferably, although not necessarily, a quantity of orthodontic adhesive 36 extends across the base 26 of the bracket 22 for securing the bracket 22 to an outer surface of the patient's tooth. Preferred adhesives 36 include photocurable adhesives, since such adhesives enable the orthodontist to precisely position the bracket on the tooth at his or her convenience and then activate a light source when desired to cure the adhesive and securely fix the bracket 22 in place.

Suitable photocurable orthodontic adhesives are described, for example, in U.S. Pat. No. 5,575,645, which is incorporated by reference herein. A particularly preferred adhesive is Transbond XT brand adhesive or Transbond LR brand adhesive, both from 3M Unitek Corporation.

The assembly 20 may alternatively include a chemical-cure adhesive such as Unite brand adhesive from 3M Unitek Corporation. In that alternative, one component of the adhesive is preapplied to the base 26 by the manufacturer and a second component is applied by the practitioner once the bracket 22 is removed from the carrier 24. For example, the base 26 may be pressed against a sponge bearing a quantity of the second component, and/or the second component is brushed on the patient's tooth surfaces.

As can be observed by reference to FIGS. 1 and 2, the base 26 of the bracket 22 extends beyond the body 28 in an occlusal and in a gingival direction. A gingival recess 38 is located between the portions of the gingival tiewings 30 and the base 26 that extend beyond the body 28 in a gingival direction, and an occlusal recess 40 is located between the portions of the occlusal tiewings 32 and the base 26 that extend beyond the body 28 in an occlusal direction. The recesses 38, 40 are often provided on conventional orthodontic brackets for use in receiving a ligature such as an elastomeric O-ring or a wire tie that is used to secure the archwire in place in the archwire slot during treatment.

The carrier 24 in the embodiment shown in FIGS. 1 and 2 includes a tubular, cylindrical member with a pair of arms 42, 44 that extend toward each other. Each of the arms 42, 44 has an outer end section, and the outer end section of the arm 42 is spaced apart from the outer end section of the arm 44 to present a channel 46 (FIG. 2) between the arms 42, 44.

The bracket 22 is located in the channel 46 and is supported by the arms 42, 44. As shown in the drawings, the end section of the arm 42 extends into the gingival recess 38 and the end section of the arm 44 extends into the occlusal recess 40. Preferably, the bracket 22 is supported by the arms 42, 44 in such a manner that the base 26 and any adhesive thereon (such as adhesive 36) is spaced from the facing section (i.e., the bottom section when viewing FIG. 1) of the carrier 24. The end sections of the arms 42, 44 may support the bracket 22 by contacting a portion of the body 28 approximately mid-way between the tiewings 30, 32 and the base 26 as shown in FIGS. 1 and 2, or alternatively may support the bracket 22 by contacting the underside of the tiewings 30, 32 (and optionally also contacting an adjacent portion of the body 28) as is likely to occur when the width of the channel 46 is larger than the width of the body 28 or when the bracket 22 is urged in a downwardly direction viewing FIGS. 1 and 2.

Optionally, the carrier 24 has an elongated, central axis and consequently may be used to support a number of brackets such as the bracket 22. Examples of additional brackets 22 are depicted in FIG. 2. The elongated carrier 24 is useful in manufacturing processes for holding the brackets 22 in an aligned array, as may be needed for inspection of the brackets 22, application of ink alignment markings to the brackets 22, or handling of the brackets 22 between manufacturing operations or during packaging. When the carrier 24 is used during manufacturing or packaging operations, it is preferable that the carrier 24 be made of a non-corrosive rigid material such as aluminum or stainless steel that can be re-used many times while satisfactorily withstanding the effects of wear and fatigue.

Figure 3:
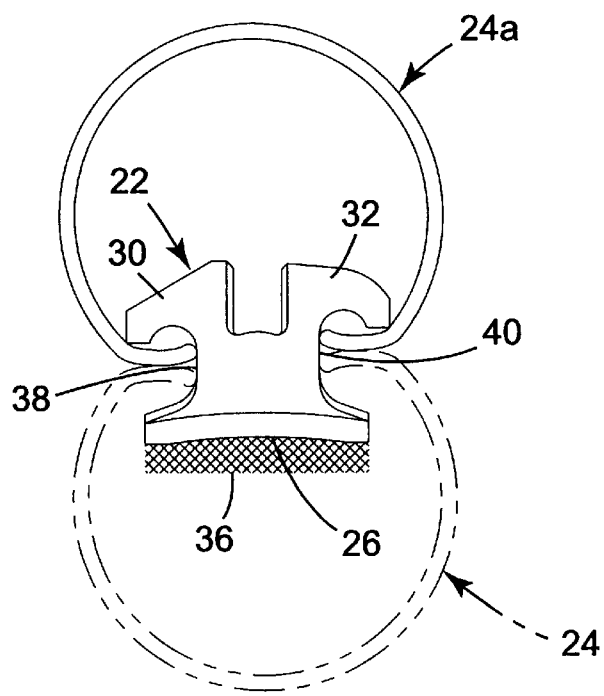
FIG. 3 is a side cross-sectional view of somewhat similar to FIG. 1 but according to another aspect of the invention wherein another carrier has been provided to transfer the brackets from the carrier shown in FIG. 2 and to support the brackets in a somewhat different manner than that which is shown in FIGS. 1 and 2 as may be desirable for certain manufacturing operations.

FIG. 3 illustrates another aspect of the invention, wherein the bracket 22 as described above is received in a channel of a second carrier 24a in an orientation opposite the orientation shown in FIGS. 1 and 2. In FIG. 3, the tiewings 30, 32 of the bracket 22 face the interior of the carrier 24a while the base 26 faces in a direction away from the carrier 24a. Optionally, the carrier 24a is identical to the carrier 24, although as an alternative it may have other configurations or may be provided with couplings for connection to automated processing equipment. Preferably, the carrier 24a is elongated and is of sufficient length to simultaneously support a number of brackets 22.

The use of the carrier 24a as shown in its orientation in FIG. 3 is beneficial for supporting the bracket 22 in a position for certain manufacturing processes, such as for brazing a mesh material to the base 26 or for applying adhesive 36 to the base 26. In one method of use of the carrier 24a, a number of brackets 22 are initially supported by the carrier 24a while the brackets 22 and the carrier 24a are simultaneously moved along the length of the channel 46 of the carrier 24 that is shown in phantom lines in FIG. 3. (Alternatively, the carrier 24 may be moved while the brackets 22 and the carrier 24a remain stationary.) The carrier 24a may then be removed from the brackets 22 by sliding the carrier 24a along the recesses 38, 40 and in a direction parallel to the mesial-distal axes of the brackets 22 until the carrier 24a is disengaged from the brackets 22. In this manner, the brackets 22 are transferred from the carrier 24a to the carrier 24 without losing their orientation relative to each other and without the necessity of handling individual brackets 22 separately.

FIG. 4 is an illustration of the assembly 20 of the bracket 22 and carrier 24 as shown in FIGS. 1 and 2 along with a container 48 and an optional holder 50. Optionally, the carrier 24 has a length along its central axis (i.e. in directions parallel to the direction of view of FIG. 4) that is slightly larger than the mesialdistal width of a single bracket 22, so that the container 48 is used for only one bracket 22. As another alternative, however, the carrier 24 is somewhat longer and supports a number of brackets 22, and the container 48 is correspondingly increased in length to enclose both the carrier 24 and all of the supported brackets 22.

The container 48 includes a substrate 52 and a cover 54 that is releasably connected to the substrate 52. Suitable materials for the substrate 52 and the cover 54 as well as suitable adhesives and other means for releasably fixing the cover 54 to the substrate 52 are described in U.S. Pat. No. 4,978,007.

The substrate 52 includes a well 56 having a central pocket 58 in the shape of a partial cylinder. The pocket 58 has a configuration that matches part of the outer surface of the carrier 24 and is preferably somewhat larger about its periphery than a semi-cylinder in order to receive the carrier 24 in snap-fit relation. Optionally, the carrier 24 may be secured to the pocket 58 by other means such as adhesives, ultrasonic welding and the like.

Preferably, the substrate 52 has a shape such that a top surface of a flange surrounding the well 56 is flush or just slightly below a reference plane that touches labial surfaces of the bracket 22. As a result, the cover 54 snugly engages the bracket 22 when the cover 54 is closed. Free movement of the bracket 22 within the container 48 is substantially hindered until such time as the cover 54 is opened. More preferably, the carrier 24 is in compression between the cover 54 and the pocket 58 when the cover 54 is closed. The carrier 24, the cover 54 and the pocket 58 thereby function as a shock absorber during shipping and handling.

The holder 50 provides convenient structure for supporting the container 48 in a chair-side tray, shelf or other location near the patient in the dental operatory. Preferably, the holder 50 is sufficiently large to support a number of containers such as the container 48, so that all of the brackets selected by the orthodontist for use on a single patient are conveniently carried by a single holder 50. For example, the holder 50 may include structure for supporting two rows of containers identical to the container 48, with ten brackets in each row so that a sufficient number of brackets are provided for all of the desired teeth according to typical orthodontic treatment procedures.

As shown in FIG. 4, the holder 50 has a groove 60 that receives and supports the container 48. Optionally, the substrate 52 has flexible outwardly extending legs 62 that are received in undercut corners of the groove 60 in snap-fit relation in order to releasably secure the container 48 to the holder 50. As other alternatives, however, the container 48 may be coupled to the holder 50 by releasable adhesives or double-sided adhesive tape, or by other structure such as hook and loop fasteners.

To remove the bracket 22 from the container 48, the cover 54 is lifted from the substrate 52 to expose the well 56. Next, the orthodontic practitioner grasps the bracket 22 by its mesial and distal sides using, for example, a pair of tweezers or other suitable hand instrument and moving the bracket 22 in an upwardly direction (viewing FIG. 4) away from the bottom of the container 48. As the bracket 22 is lifted, the outer end sections of the carrier arms 42, 44 engage the labial side of the bracket base 26, and further upward movement causes the arms 42, 44 to deflect outwardly in directions away from each other. Additional movement of the bracket 22 in an upwardly direction causes the arms 42, 44 to spread apart and enlarge the channel 46 to a dimension that is equivalent to the occlusal-gingival width of the bracket base 26, so that the bracket 22 can then be pulled completely free of and disengage the carrier 24.

In the embodiment shown in FIG. 4, the carrier 24 is preferably made of a flexible material that can readily deform to allow spreading movement of the arms 42, 44 and yet have sufficient resilience and rigidity to hold the bracket 22 securely against the underside of the cover 54 when the cover 54 is closed. Preferred materials for the carrier 24 include, for example, polyethylene or polypropylene. Optionally, the arms 42, 44 of the carrier 24 are provided with lines of weakness 64 such as grooves, perforations, slits, apertures or recesses on either or both of their interior and exterior surfaces, to facilitate spreading and folding back of the arms 42, 44 when the bracket 22 is lifted from the container 48. The lines of weakness 64 may cause the material to fracture, or alternatively may facilitate stress of the material past its yield point as the arms 42, 44 are moved apart. The lines of weakness 64 hinder return movement of the arms 42, 44 to their orientation shown in FIG. 4 and preferably prevent substantially all such return movement. As another option, however, the carrier 24 may be made of a dead-soft material such as aluminum. The lines of weakness 64 or, alternatively, the dead-soft material help ensure that the arms 42, 44 do not engage and disturb the adhesive 36 as the bracket 22 is removed from the container 48.

Figure 6:
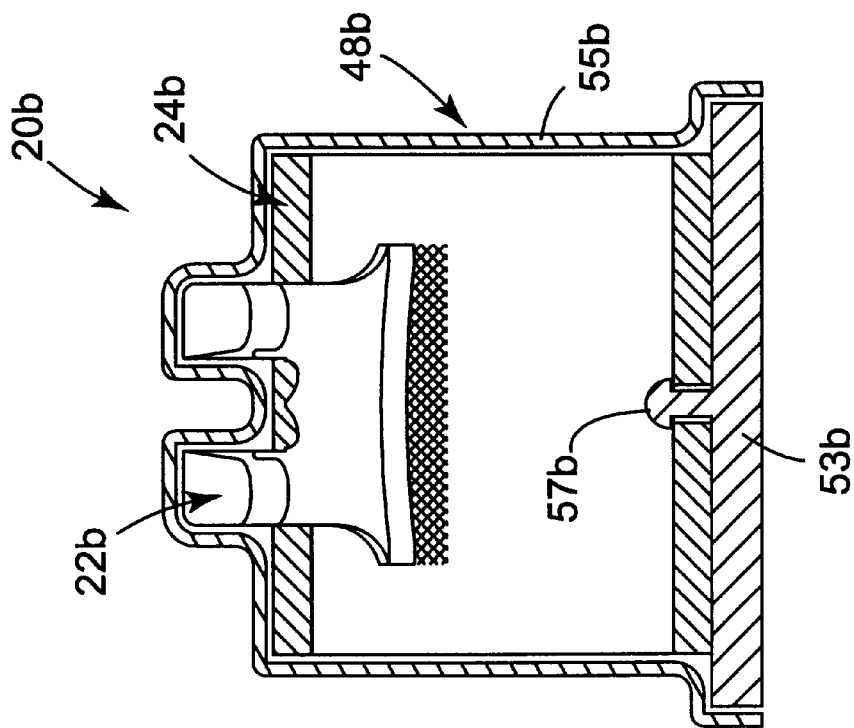
FIG. 6 is an end cross-sectional view of the bracket, carrier and container assembly depicted in FIG. 5.
Figure 5:
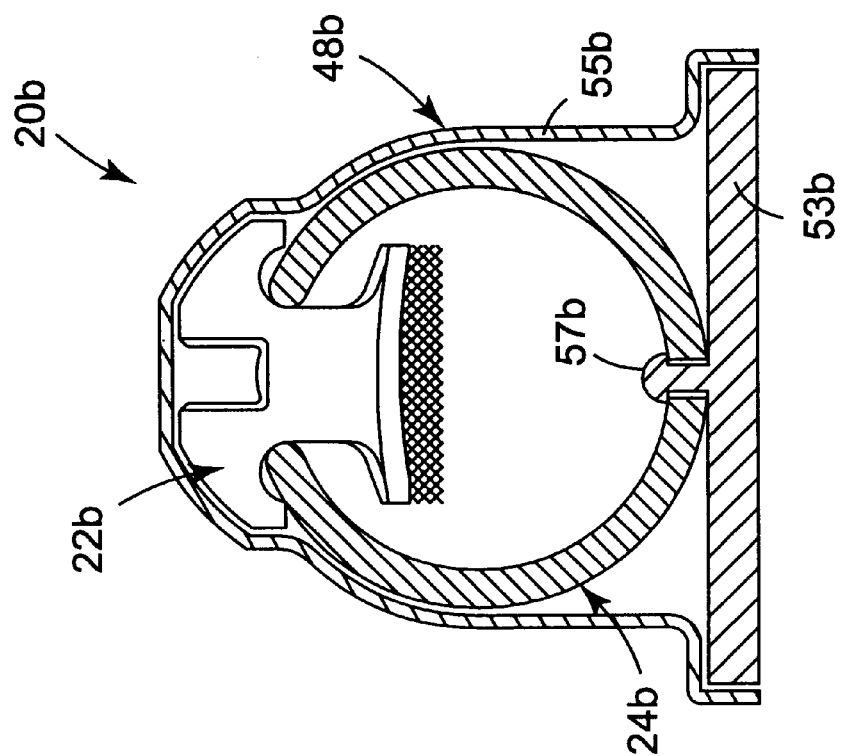
FIG. 5 is a view of an orthodontic bracket and carrier assembly according to another embodiment of the invention, wherein the carrier includes at least one aperture and a container surrounding the carrier and the bracket includes a peg received in the aperture.

FIGS. 5 and 6 show another embodiment of the invention, wherein an assembly 20b includes an orthodontic bracket 22b and a carrier 24b. The bracket 22b is identical to the bracket 22 described above. The carrier 24b is identical to the carrier 24, except that a bottom portion of the carrier 24b (viewing FIGS. 5 and 6) includes an aperture that is optionally circular.

The assembly 20b also includes a container 48b having a base 53b and a barrier 55b connected to the base 53b. The base 53b is preferably relatively rigid and includes an upstanding peg 57b that extends through the aperture on the bottom of the carrier 24b. The top of the peg 57b includes an enlarged head that is bigger than the aperture in order to securely connect the carrier 24b to the base 53b. The head of the peg 57b could be formed, for example, by an ultrasonic welding operation or by a heated platen.

Preferably, the barrier 55b is a vacuum formed or heat sealed over the bracket 22b and the carrier 24b as well as the base 53b in order to hinder movement of the bracket 22b relative to the carrier 24b. The barrier 55b may be made of a thin plastic sheet material such as polyester film that can be readily cut or fractured when desired to remove the bracket 22b. Optionally, the barrier 55b is made of a material such as described in U.S. Pat. No. 4,978,007 that transmits light in the visible spectrum and yet is substantially opaque to actinic radiation. As such, the bracket 22b is visible through the barrier 55b in order to check the contents of the assembly 20b, and yet the photocurable adhesive on the bracket 22b will not unduly cure before such time as the container 48b is opened.

The apertures of the carrier 24b provide an advantage during manufacture. When such apertures are spaced at regular intervals along the length of the carrier 24b, the apertures provide a convenient series of holes for sprocket tractor feed systems as may be utilized in moving the bracket 22b from one processing station to another, or from a processing station to a packaging station. Further, more than one aperture may be provided for each corresponding bracket 22b, and the apertures may be of shapes other than circular in order to facilitate securing the carrier 24b to a transport device in the factory or to the base 53b of the container 48b. If desired, the apertures can provide automated feedback to a computer or controller as to the position of each bracket 22b along the manufacturing line and can serve to count the number of brackets 22b that have passed a certain location along the manufacturing line.

FIG. 7 depicts an orthodontic assembly 20c according to another embodiment of the invention. The assembly 20c includes one or more brackets 22c (three brackets 22c are shown in FIG. 7) that are substantially identical to the brackets 22. The carrier 24c is identical to the carrier 24b with the exceptions as described below.

As illustrated in FIG. 7, the carrier 24c has a channel 46c with a series of rectangular notches 47c that are optionally located opposite respective apertures 49c. Each notch 47c corresponds in shape to the perimeter configuration of the bracket body and provides a nest to receive and support the respective bracket 22c. The notches 47c complementally engage the bracket body and hinder unintentional sliding movement of the brackets 22c along the channel 46c.

Another embodiment of the invention is illustrated in FIG. 8, wherein an orthodontic assembly 20d includes a series of orthodontic brackets 22d, each of which is essentially identical to the bracket 22 described above. The assembly 20d also includes a carrier 24d that is similar to the carriers 24, 24b and 24c with the exceptions as described below.

In more detail, the carrier 24d includes a series of slits or relief areas 51d located along each side of the channel 46d. As such, arms 42d, 44d of the carrier 24d are segregated into arm portions 43d that deflect and move somewhat independently of movement of adjacent arm portions 43d. The relief areas 51d facilitate removal of a selected one of the brackets 22d, without unduly spreading the arms 42d, 44d to such an extent that adjacent brackets 22d located along the channel 46d might otherwise move from their intended location.

Figure 9:
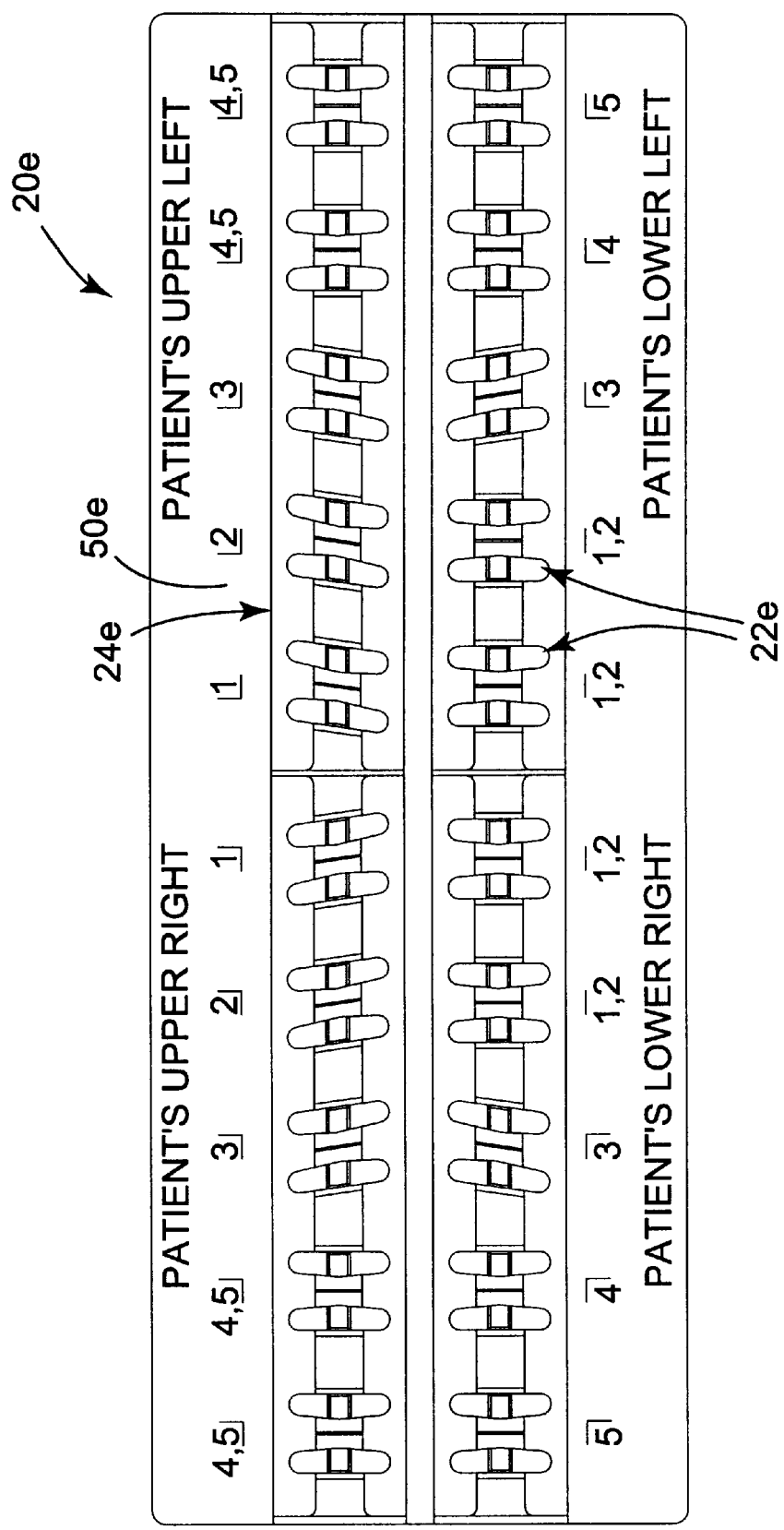
FIG. 9 is a plan view of a pair of carriers and a number of brackets received in the carriers according to a further embodiment of the invention, wherein the carriers are received in a chair-side tray.

FIGS. 9 and 10 illustrate an assembly 20e according to yet another embodiment of the invention. The assembly 20e includes a series of orthodontic brackets 22e that are received in carriers 24e. The assembly 20e also includes a chair-side set-up tray or holder 50e having two elongated, parallel, side-by-side grooves.

The brackets 22e are similar to the brackets 22 described above. The carrier 24e is somewhat similar to the carrier 24d shown in FIG. 8, except that the carrier 24e has a rectangular configuration in directions transverse to its longitudinal axis as can be appreciated by reference to FIG. 10. The two grooves of the holder 50e matingly receive the carriers 24e and securely hold the latter in place. The carriers 24e may be secured in the holder 50e by double-sided adhesive tape with a releasable adhesive, or by mating dovetail shapes of the carriers 24e and grooves of the holder 50e that provide a snap-fit, secure connection.

The brackets 22e are released from the carrier 24e by grasping the mesial and distal sides of the brackets 22e with a hand instrument and lifting the bracket 22e in a direction away from the holder 50e. Alternatively, the brackets 22e may be sequentially released from the carrier 24e by sliding each bracket 22e along the length of the channel and toward an open end of the carrier 24e.

The assembly 20e that is depicted in FIGS. 9 and 10 represents a set or case of brackets as may be useful for a single patient. Preferably, the carriers 24e with selected brackets 22e are shipped to the orthodontist who then places the carriers 24e in the appropriate grooves of the holder 50e. As an alternative, the carriers 24e may be placed in the holder 50e by the manufacturer and shipped with the holder to the practitioner. In either instance, the carriers 24e are preferably placed in a hermetically sealed container that is opaque to actinic radiation before shipment to the practitioner in order to extend the shelf life of the light-curable adhesive and help keep the brackets 22e free of dust and other contaminants. Optionally, a stop member such as a section of low adhesion adhesive tape is placed across each end of the channel of each carrier 24e to help preclude the brackets 22e from sliding along the channel and inadvertently disengaging from the carrier 24e.

The orthodontic assembly 20f that is shown in part in FIG. 11 includes a carrier 24f that is somewhat similar to the carrier 24, except that the carrier 24f has a key 59f that extends in a direction parallel to the central axis of the carrier 24f and to the mesial-distal axis of a bracket 22f (that is identical to the bracket 22). The key 59f is located on the bottom of the carrier 24f and is remote from ends of arms 42f, 44f.

A container 48f for receiving the carrier 24f includes a well 56f having a keyway 61f. The key 59f is received in the keyway 61f in snap-fit relation, and is precluded from rotating relative to the keyway 61f due to its elongated and rectangular configuration in plan view (not shown). Although remaining components of the container 48f, it should be understood in this regard that such components may be similar or identical to corresponding components set out in the embodiments described above.

An orthodontic assembly 20g as shown in FIG. 12 includes an orthodontic bracket 22g and a carrier 24g. Except as described below, the bracket 22g and the carrier 24g are essentially identical to the brackets and carriers described above.

The carrier 24g has somewhat "figure 8"-shaped configuration, with opposed sides of the carrier 24g touching each other as shown at the locations 25g. When the practitioner squeezes the convex, bulbous sides of the carrier 24g at the locations designated by the numeral 27g, opposed sides of the carrier 24g pivot about the engagement points 25g and tend to spread arms 42g, 44g in order to facilitate removal of the bracket 22g from the carrier 24g.

The orthodontic assembly 20h depicted in FIG. 13 is somewhat similar to the orthodontic assembly 20g, except that a lower portion of a carrier 24h has two diverging sections as indicated by the numerals 29h. When the sections 29h are squeezed together by the practitioner's fingers, arms 42h, 44h of the carrier 24h tend to spread apart and facilitate disengagement and removal of the bracket 22h from the carrier 24h.

Figure 14:
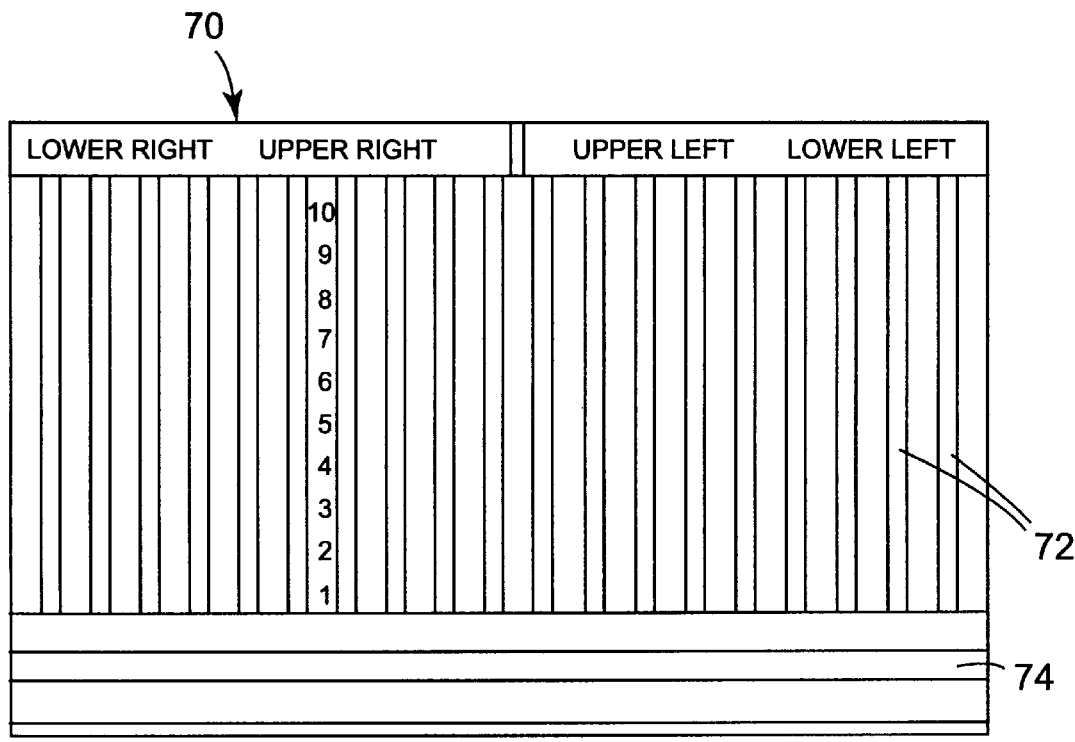
FIG. 14 is a front elevational view of a stand especially suitable for use with certain of the carriers described above.
Figure 15:
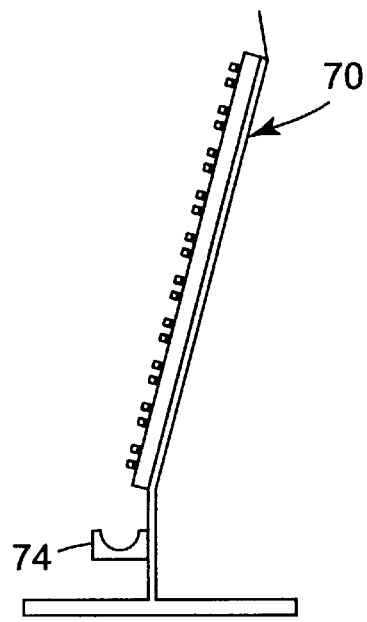
FIG. 15 is a side elevational view of the stand shown in FIG. 14.

FIGS. 14 and 15 illustrate a stand 70 that is particularly useful with the orthodontic assemblies described above. The stand 70 includes a number of channels 72 (see FIG. 14) that extend in parallel upright directions and each channel 72 is adapted to releasably receive a carrier supporting a number of brackets (shown only in FIG. 15). The stand 70 provides a convenient inventory dispensing system so that the user can readily determine how many brackets are on hand. Optionally, a cutter (not shown) is coupled to the stand 70 for cutting the carrier between adjacent brackets for custom tray set-ups. The cut portion of the carrier along with the bracket then drop to the underlying trough 74. As another option, the brackets move freely along the channels of the carriers so that as a bracket is removed from the lowermost end of each carrier the remaining brackets in the carrier slide downwardly until the next adjacent bracket reaches the lowermost end.

Optionally, structures such as a proximity sensor are associated with each channel 72 and connected to a computer in order to determine the amount of brackets remaining in each carrier. Moreover, the carriers could include bar codes that are scanned to provide information to the computer, so that the practitioner may readily determine both the quantity and identity of the brackets in inventory. Such structure can be used to determine usage habits and facilitate re-ordering of the brackets when necessary.

Figure 16:
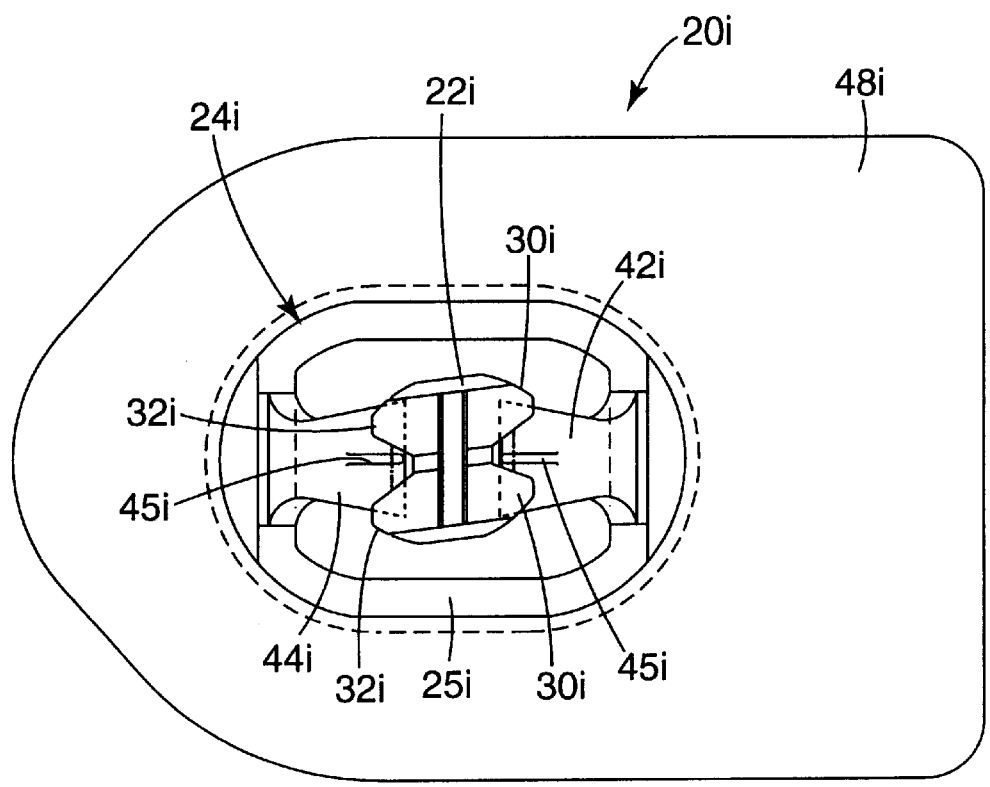
FIG. 16 is a plan view of an assembly that includes an orthodontic bracket, a carrier for the bracket and a container for the bracket and carrier according to another embodiment of the invention.
Figure 17:
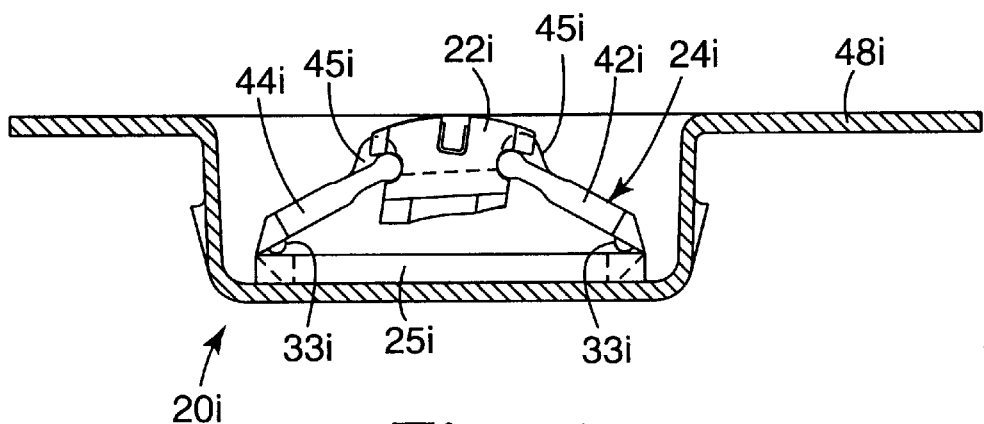
FIG. 17 is a side cross-sectional view of the assembly shown in FIG. 16.

The orthodontic assembly 20i that is shown in FIGS. 16 and 17 includes a bracket 22i, a carrier 24i supporting the bracket 22i and a container 48i that surrounds the carrier 24i and the bracket 22i. Preferably, the container 48i includes a cover (not shown) that is similar to the covers described above. The carrier 24i includes a pair of arms 42i, 44i that releasably engage a gingival recess and an occlusal recess respectively of the bracket 22i.

The carrier 24i has a ring-shaped bottom section 25i that is secured to a base of the container 48i by adhesive, welding or other suitable means. In turn, the arms 42i, 44i are connected to the bottom section 25i. Alternatively, the bottom section 25i could be omitted and the arms 42i, 44i connected to the base or the sides of the container 48i, and optionally the arms 42i, 44i are integral with the container 48i.

In the embodiment of the assembly 20i illustrated in FIGS. 16 and 17, the arms 42i, 44i are connected to the bottom section 25i by a living hinge that permits movement of the arms 42i, 44i in arcs away from each other as the bracket 22i is lifted from the container 48i. The carrier 24i preferably includes one or more retention bumps 33i next to the bottom of the arms 42i, 44i that help restrain the arms 42i, 44i and consequently the bracket 22i against undue movement until such time as the container 48i is opened. Optionally, small tack welds could be provided by a heated blade or the like near the base of the arms 42i, 44i and near the living hinge to temporarily retain the arms 42i, 44i in their orientations shown in FIG. 17 until such time as the bracket 22i is removed from the container 48i. Preferably, when the cover is in place extending over the top of the container 48i, the bottom of the cover contacts the labial side of the tiewings of the bracket 22i and more preferably exerts a slight pressure on the tiewings in order to further help assure that the bracket 22i does not unduly shift from its orientation as shown in FIGS. 16 and 17.

Preferably, the carrier 24i is made of a unitary section of material such as stiff plastic material that is compatible with the adhesive. Suitable plastic materials include, for example, polyester, polypropylene, acetate and polyethylene. The living hinges are made of thin plastic webs that enable the arms 42i, 44i to easily move relative to the bottom section 25i. As an alternative to the living hinge, the carrier 24i may be provided with other types of hinge structure or preferential fold lines or weakness lines including grooves, slits, perforations, apertures, recess or the like. Preferably, the arms 42i, 44i are biased outwardly away from each other and do not tend to move in return arcs as the bracket 22i is disengaged from the outer end sections of the arms 42i, 44i so as not to disturb an adhesive that is optionally coated onto the base of the bracket 22i by the manufacturer.

Preferably, the carrier 24i is preferably initially flat and bent to the configuration shown in FIGS. 16–17. Preferably, the carrier 24i is resilient, and may be molded as an initially flat piece or die cut from a flat section of sheet material. When the arms 42i, 44i are bent to the orientation shown in FIGS. 16–17, the arms 42i, 44i tend to self-open in arcs away from each other as the practitioner lifts the bracket 22i and ruptures any tack welds temporarily holding the arms 42i, 44i stationary. Such construction helps insure that the arms 42i, 44i do not tend to self-close (i.e. move toward each other) so that any adhesive on the base of the bracket 22i is not disturbed.

Preferably, an upper side of the outer end section of at least one of the arms 42i, 44i is provided with an upstanding tab 45i. As shown in the illustrated embodiment, the tab 45i of the arm 42i is received in the space between gingival tiewings 30i, while the tab 45i of the arm 44i is received in the space between occlusal tiewings 32i. The tabs 45i help prevent lateral movement of the bracket 22i in a mesial or distal direction until such time as the cover of the container 48i is opened and the bracket 22i is lifted to disengage the arms 42i, 44i.

Figure 18:
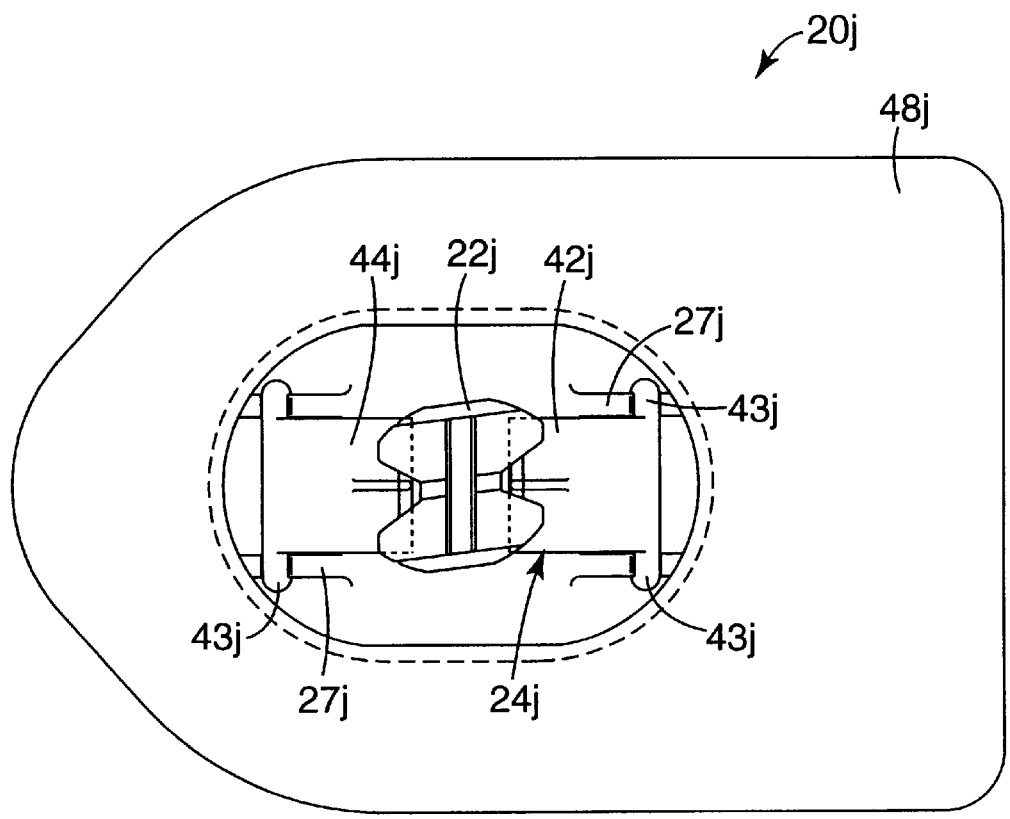
FIG. 18 is a view somewhat similar to FIG. 16 except in accordance with another embodiment of the invention.
Figure 19:
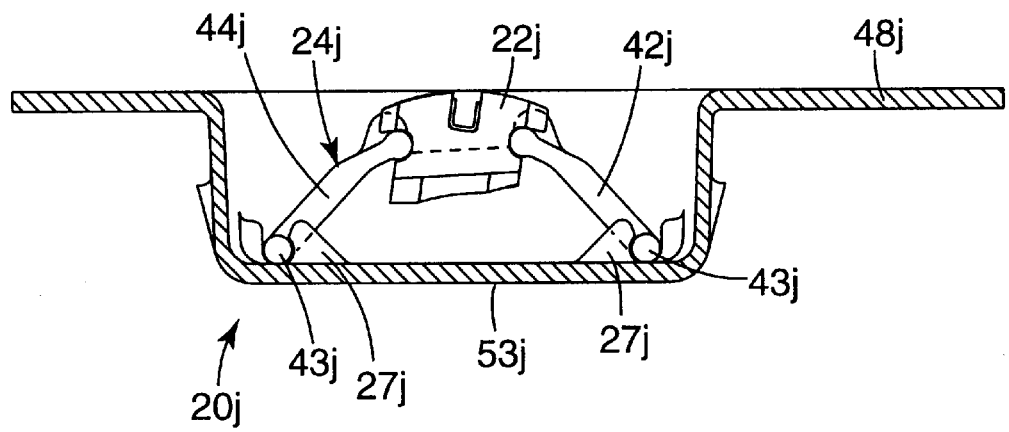
FIG. 19 is a side cross-sectional view of the assembly illustrated in FIG. 18.

The embodiment of the invention that is illustrated in FIGS. 18 and 19 includes an assembly 20*j* that is somewhat similar to the assembly 20*i*, in that the assembly 20*j* includes an orthodontic bracket 22*j*, a carrier 24*j* and a container 48*j*. The carrier 24*j* includes two arms 42*j*, 44*j* that releasably engage a gingival recess and an occlusal recess of the bracket 22*j*. Preferably, each arm 42*j*, 44*j* includes an upstanding tab similar to the tabs 45*i* mentioned above. However, the carrier 24*j* includes a mechanical hinge instead of a living hinge for facilitating swinging movement of the arms 42*j*, 44*j* in respective arcs as the bracket 22*j* is lifted from the container 48*j*.

In more detail, the carrier 24*j* includes two pair of hinge sections 27*j* that are preferably integrally molded to a base 53*j* of the container 48*j*. Additionally, a lower end section of the arms 42*j*, 44*j* remote from the upper, outer end sections each have an opposed pair of outwardly extending pins 43*j*, each of which is received in a respective one of the hinge sections 27*j*. Preferably, the pins 43*j* are constructed of a size to snap-fit into the hinge sections 27*j* to simplify assembly and to also help ensure that the arms 42*j*, 44*j* do not uncouple from the container 48*j* as the bracket 22*j* is lifted from the container 48*j*.

Figure 20:
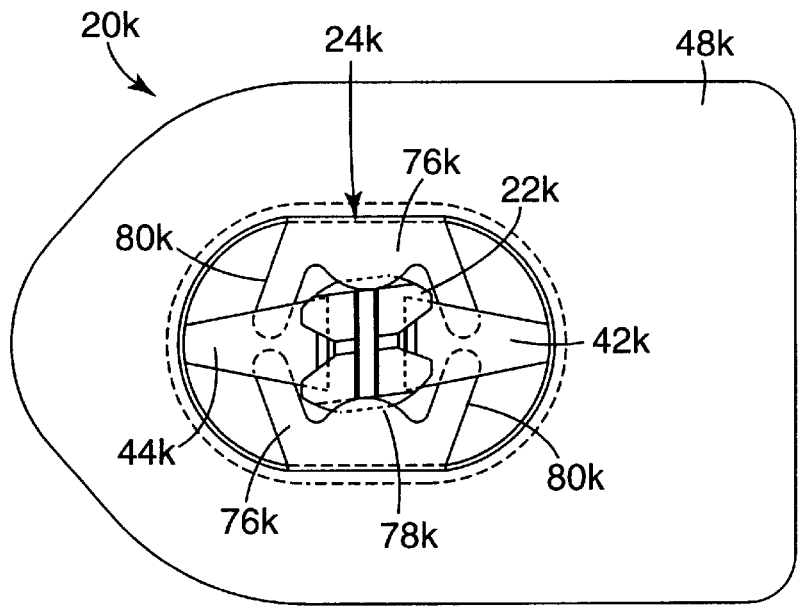
FIG. 20 is a plan view of an assembly somewhat similar to FIG. 16 except in accordance with yet another embodiment of the invention.
Figure 21:
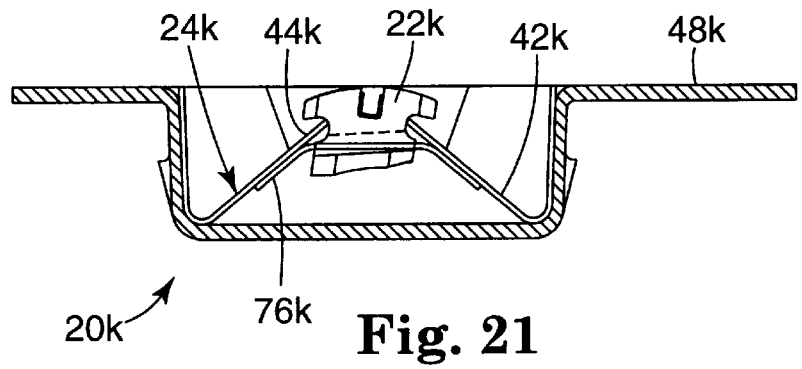
FIG. 21 is a side cross-sectional view of the assembly depicted in FIG. 20.
Figure 22:
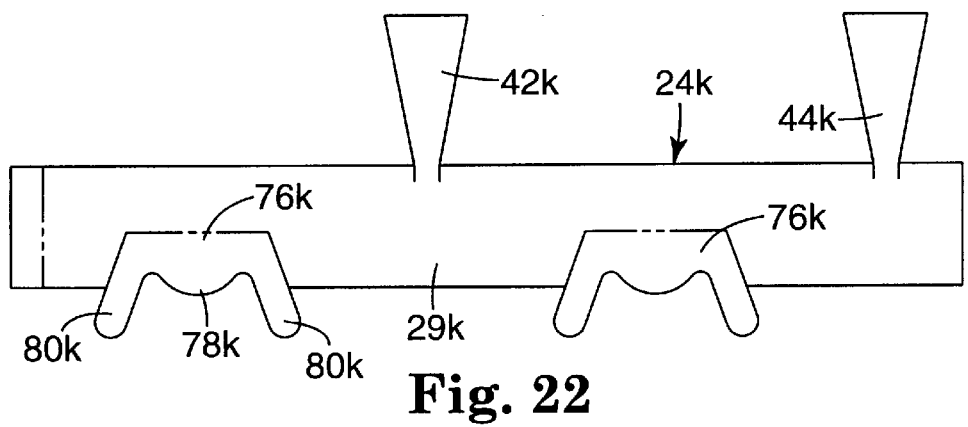
FIG. 22 is a view of a carrier of the assembly shown in FIGS. 20 and 21 as it appears before it is placed a container of the assembly.

The orthodontic assembly 20*k* that is illustrated in FIGS. 20–22 according to another embodiment of the invention includes a bracket 22*k*, a carrier 24*k* and a container 48*k*. The bracket 22*k* and the container 48*k* are substantially similar to the brackets and containers described above. However, the carrier 24*k* is somewhat different than the previously described carriers, in that the carrier 24*k* provides a somewhat different cradle for releasably supporting the bracket 22*k*.

FIG. 22 is an illustration of the carrier 24*k* as it initially appears in a flat orientation before it is shaped into an oval and placed in the container 48*k*. The carrier 24*k* includes a wall section 29*k* as well as two arms 42*k*, 44*k*. In addition, the carrier 24*k* includes a pair of supports 76*k*, each of which has a middle section 78*k* and a pair of leg sections 80*k* located on opposite sides of the middle section 78*k*. The carrier 24*k* is preferably die cut from a flat sheet of material such as plastic or metal, but may also be molded if desired. Optionally, the arms 42*k*, 44*k* may be provided with tabs similar to the tabs 45*i* described above. As an additional option, the middle sections 78*k* may also be provided with upstanding tabs for reception into the archwire slot openings on the mesial and distal sides of the bracket 22*k*.

As depicted in FIGS. 20 and 21, the wall section 29*k* of the carrier 24*k* extends around the oval-shaped peripheral wall of the container 48*k*, and the arms 42*k*, 44*k* engage a gingival recess and an occlusal recess respectively of the bracket 22*k*. Preferably, the wall section 29*k* is fixed to the sidewall of the container 48*k* by an adhesive, by welds or other suitable means to ensure that the carrier 24*k* remains coupled to the container 48*k*.

The middle sections 78*k* of the supports 76*k* engage the mesial side and distal side of the bracket 22*k* to help prevent lateral movement of the bracket 22*k* in a mesial or distal direction. As shown in FIG. 20, the leg sections 80*k* of the supports 76*k* are received beneath the arms 42*k*, 44*k* when the bracket 22*k* is in the container 48*k*. As the bracket 22*k* is lifted from the container 48*k*, the leg sections 80*k* engage the arms 42*k*, 44*k* and help to ensure that the arms 42*k*, 44*k* move upwardly and open outwardly to enable the bracket 22*k* to be released from the carrier 24*k*. As shown by the dashed lines in FIG. 20, the base of the bracket 22*k* extends outwardly in a mesial and distal direction past the overlying tiewings respectively and engage the middle sections 78*k* of the supports 76*k* as the bracket 22*k* is lifted from the container 48*k*, in order to facilitate swinging, opening movement of the supports 76*k* as well as opening movement of the arms 42*k*, 44*k*. Alternatively, the leg sections 80*k* could be received above the arms 42*k*, 44*k*.

As an alternative to the construction shown in FIGS. 20–22, the arms 42*k*, 44*k* and the supports 76*k* could be attached directly to the sides or to the base of the container 48*k*, or could be integrally molded with the sides or the base of the container 48*k*. As yet another alternative, the carrier 24*k* could include four discreet wall sections that are in turn connected to the side wall or the base of the container 48*k*. In that alternative, each of the wall sections is connected to one of the arms 42*k*, 44*k* or one of the supports 76*k*.

The embodiment of the invention that is shown in FIGS. 23–26 includes an orthodontic assembly 20*m* that is somewhat similar to the assembly 20*k* described above, in that the assembly 20*m* includes a bracket 22*m* (not shown in FIG. 25), a folded carrier 24*m* and a container 48*m*. However, the carrier 24*m* has a somewhat cross-shaped configuration that is different than the configuration of the carrier 24*k* illustrated in FIGS. 20–22.

In more detail, the carrier 24*m* has a central section 31*m* that is integrally connected to two arm sections 42*m*, 44*m* as well as to two supports 76*m*. Each of the arms 42*m*, 44*m* includes a middle section 78*m* and a pair of leg sections 80*m* located on the opposite sides of the middle section 78*m*. Preferably the central section 31*m* is securely connected to the base of the container 48*m* by an adhesive, by tack welds or by other suitable means.

FIG. 26 shows the carrier 24*m* before it is folded and placed in the container 48*m*. Once in place in the container 48*m*, the arms 42*m*, 44*m* and the supports 76*m* fold inwardly to present a cradle for releasably supporting the bracket 22*m*. As the bracket 22*m* is lifted from the container 48*m*, each of the arms 42*m*, 44*m* and each of the supports 76*m* swing outwardly in respective arcs until opened sufficiently to permit disengagement of the bracket 22*m* from the carrier 24*m*.

Figure 27:
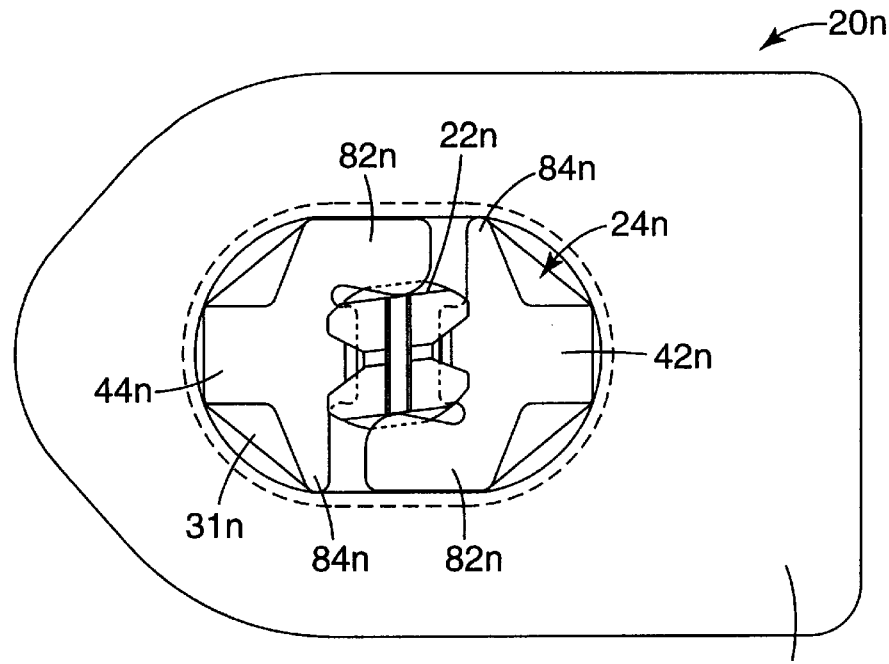
FIG. 27 is a plan view of an orthodontic assembly that includes a bracket, a carrier and a container in accordance with another embodiment of the invention.
Figure 28:
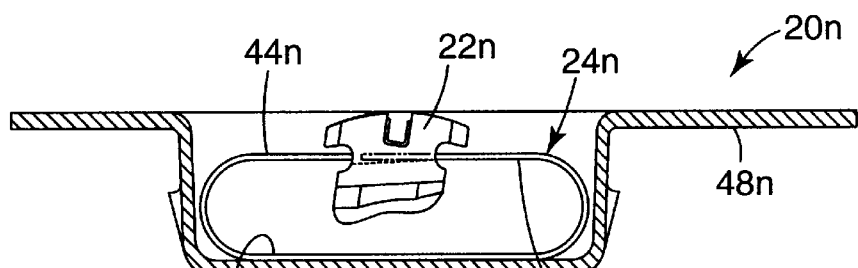
FIG. 28 is a side cross-sectional view of the assembly shown in FIG. 27.
Figure 29:
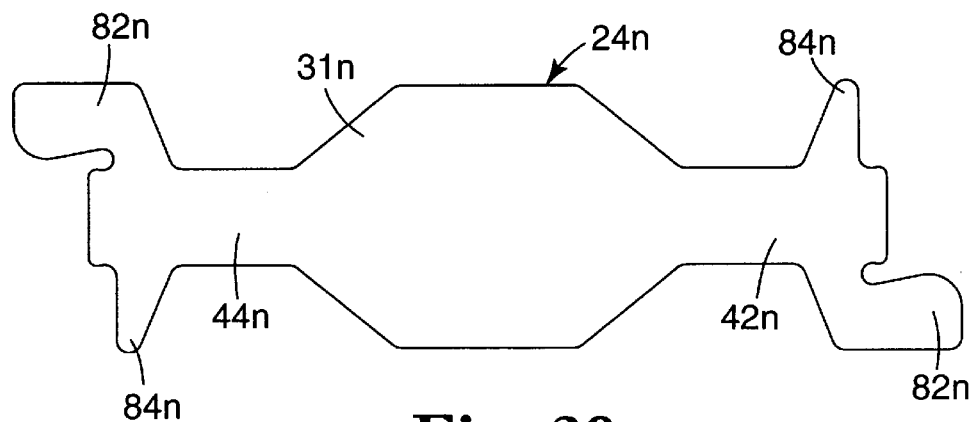
FIG. 29 is an illustration of a carrier of the assembly depicted in FIGS. 27–28 showing the carrier as it appears before it is placed in a container of the assembly.

An orthodontic assembly 20*n* according to another embodiment of the invention is shown in FIGS. 27–29. The assembly 20*n* includes a bracket 22*n*, a carrier 24*n* and a container 48*n*. The bracket 22*n* and the container 48*n* are preferably the same or similar to the brackets and the containers described above.

The carrier 24*n* has a central section 31*n* as well as two arms 42*n*, 44*n* that are preferably integrally connected to the central section 31*n*. Preferably, the carrier 24*n* initially appears as shown in FIG. 29, and is die cut from a sheet of plastic material. The central section 31*n* is secured to a base of the container 48*n* by an adhesive, by tack welding or by other means. Once the carrier 24*n* is in place in the container 48*n*, the carrier 24*n* forms a folded cradle for releasably supporting the bracket 22*n*.

The arms 42*n*, 44*n* each have a middle section that engages a gingival recess and an occlusal recess respectively of the bracket 22*n*. As shown in FIG. 27, each arm 42*n*, 44*n* also includes a side section 82*n* that engages the mesial side or the distal side respectively of the bracket 22*n*. Additionally, each of the arms 42*n*, 44*n* includes an end section 84*n* that contacts an adjacent side wall of the container 48*n* in order to facilitate stability of the carrier 24*n* and unintentional movement of the bracket 22*n* when received in the container 48*n*.

Figure 31:
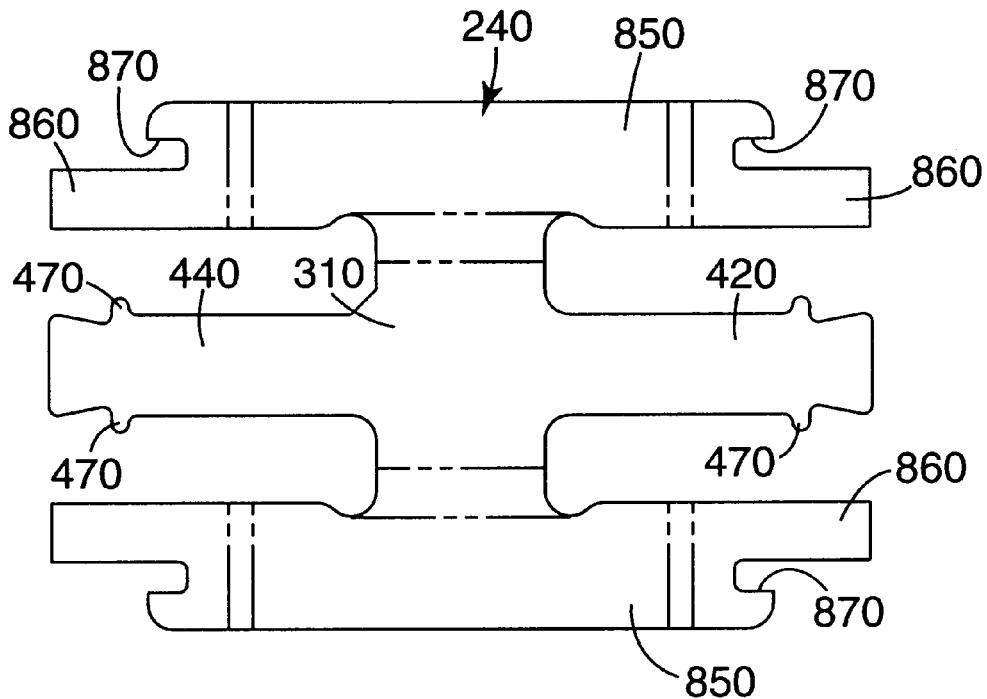
FIG. 31 is an illustration of a carrier of the assembly depicted in FIG. 30 as it appears before it is placed in a container of the assembly.
Figure 30:
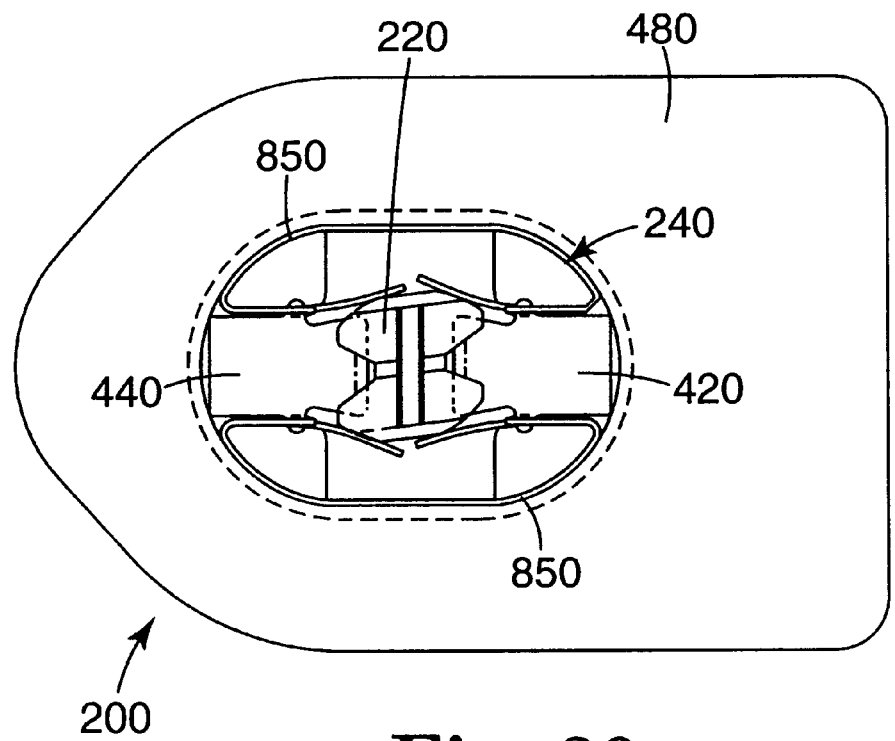
FIG. 30 is a plan view of an orthodontic assembly that includes a bracket, a carrier and a container in accordance with another embodiment of the invention.

The orthodontic assembly 20*o* that is illustrated in FIGS. 30 and 31 also includes a bracket 20*o* and a container 48*o* that is either the same or preferably similar to the brackets and containers described previously. The assembly 20o also includes a carrier 24o for releasably supporting the bracket 22o while received in the container 48o.

The carrier 24o is preferably die cut from a sheet of suitable material such as plastic film, although other materials are also possible. The carrier 24o as it preferably initially appears before connection to the container 48o has a flat configuration is shown in FIG. 31. The carrier 24o includes a central section 31o and two arms 42o, 44o that extend outwardly in opposite directions from the central section 31o.

Additionally, the carrier 24o includes a pair of lateral sections 85o that extend outwardly away from each other in opposite directions from the central section 31o and in directions perpendicular to the directions of extension of the arms 42o, 44o. Each of the lateral sections 85o includes a pair of outermost end pieces 86o as well as a notch 87o adjacent each end piece 86o.

The central section 31o is preferably secured to the base of the container 48o by adhesive, tack welding or other suitable means. As shown in FIG. 30, the lateral sections 85o are folded upwardly and extend around part of the side wall of the container 48o, such that the end pieces 86o engage mesial and distal sides of the bracket 22o. Preferably, the end pieces 86o engage mesial and distal sides of the base of the bracket 22o, although engagement with the tiewings of the bracket 22o is also possible.

Each of the arms 42o, 44o includes a pair of outwardly extending protrusions 47o. When the carrier 24o is received in the container 48o, each of the protrusions 47o is received in a respective one of the notches 87o as shown in FIG. 30. Reception of the protrusions 47o in the notches 87o facilitates the stability of the carrier 24o and helps insure that the arms 42o, 44o do not spring outwardly until such time as the practitioner removes the bracket 22o from the container 48o.

Figure 32:
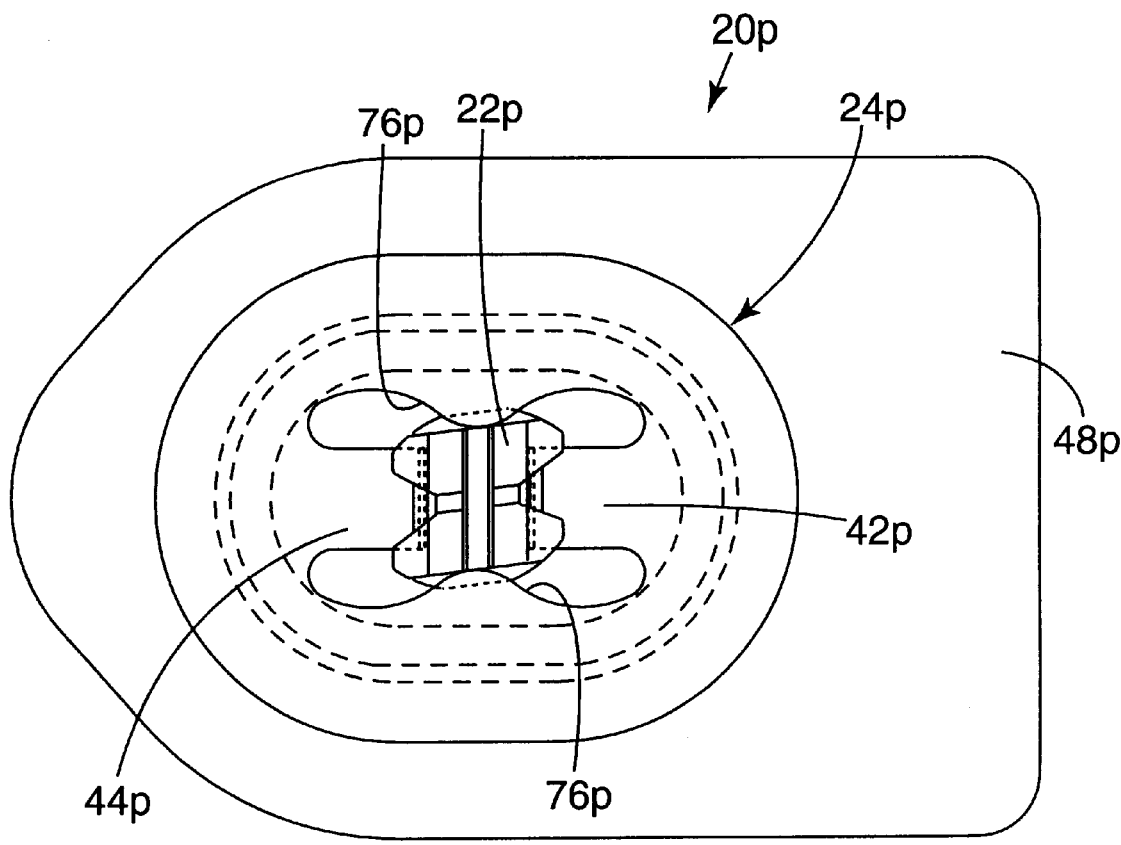
FIG. 32 is a plan view of an orthodontic assembly that includes a bracket, a carrier and a container according to yet another embodiment of the invention.
Figure 33:
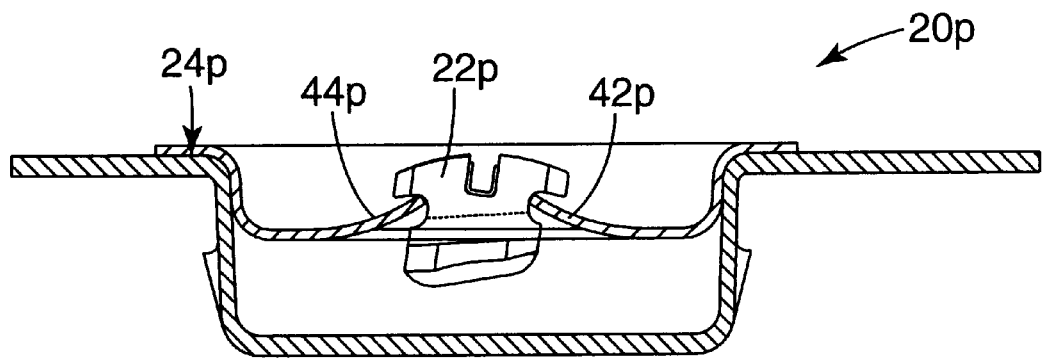
FIG. 33 is a side cross-sectional view of the assembly shown in FIG. 32.

An orthodontic assembly 20p according to another embodiment of the invention is shown in FIGS. 32 and 33, and includes a bracket 22p and a container 48p that are preferably the same or similar to the brackets and containers mentioned above. However, the carrier 24p is somewhat different from the abovedescribed carriers, in that the carrier 24p has a somewhat cup-shaped configuration and is preferably supported in suspended fashion from the top of the container 48p as can be observed by reference to FIG. 33. Preferably, the carrier 24p is securely fixed to the container 48p by adhesive, tack welding or other suitable means. Optionally, the carrier 24p is integrally molded with the container 48p.

The carrier 24p has a pair of arms 42p, 44p that are received in a gingival recess and an occlusal recess of the bracket 22p. Moreover, the carrier 24p has a pair of supports 76p that engage mesial and distal sides of the bracket 22p.

As the bracket 22p is lifted from the container 48p, the arms 42p, 44p as well as the supports 76p deflect and move outwardly away from each other to enable the bracket 22p to be released from the carrier 24p. Optionally, the carrier 24p includes lines of weakness (similar to those described above) to help avoid self-return of the arms 42p, 44p and the supports 76p to their respective orientations as shown in FIGS. 32–33 as the bracket 22p is lifted from the container 48p. Such lines of weakness help to insure that the arms 42p, 44p and the supports 76p do not contact and disturb adhesive on the base of the bracket 22p as the bracket 22p is removed from the container 48p.

Figure 34:
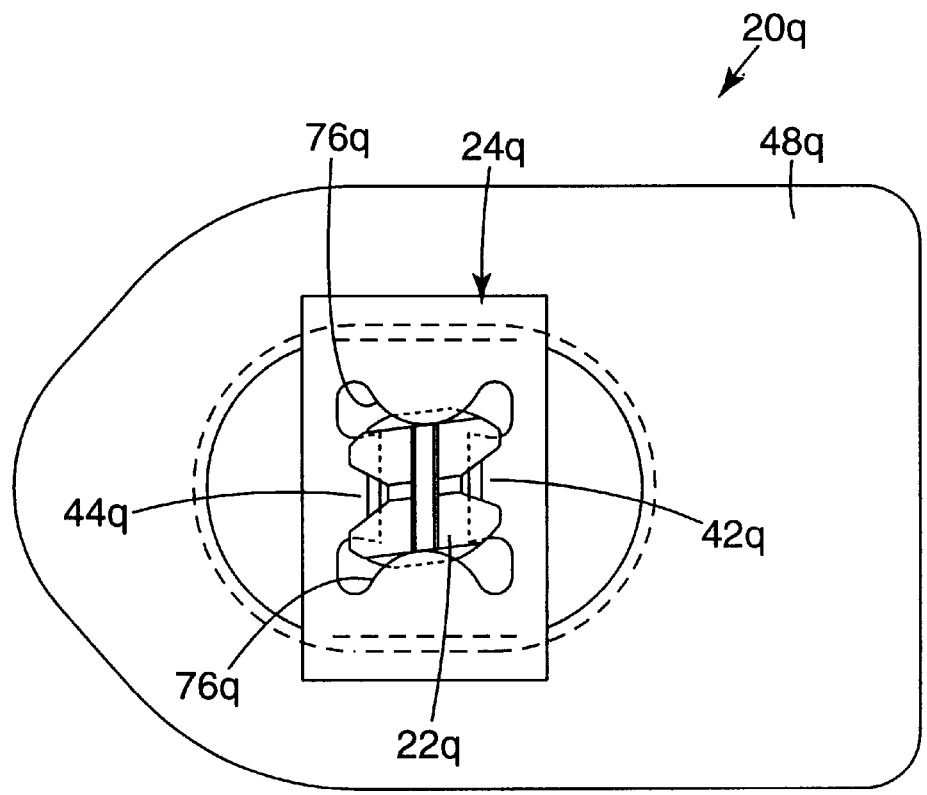
FIG. 34 is a plan view of an orthodontic assembly that includes a bracket, a carrier and a container according to a further embodiment of the invention.
Figure 35:
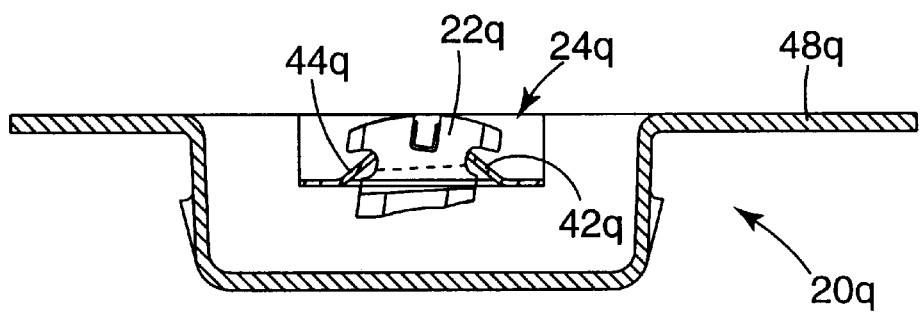
FIG. 35 is a side cross-sectional view of the assembly shown in FIG. 34.

An orthodontic assembly 20q according to yet another embodiment of the invention is shown in FIGS. 34 and 35, and includes a bracket 22q and a container 48q that are preferably the same or similar to the brackets and containers described above. Moreover, the carrier 24q is somewhat similar to the carrier 24p, in that the carrier 24q also includes movable arms 42q, 44q and supports 76q that releasably engage recesses and sides of the bracket 22q.

However, the carrier 24q has an overall rectangular configuration in plan view as shown in FIG. 34 and is suspended from opposite sides of the top of the container 48q. For example, the carrier 24q may be essentially draped and have a somewhat U-shaped configuration in a cross-sectional view that is perpendicular to both of the views of FIGS. 34 and 35. The carrier 24q has two arms 42q, 44q as well as two supports 76q that releasably hold the bracket 22q in the container 48q until such time as the bracket 22q is lifted from the container 48q.

Figure 36:
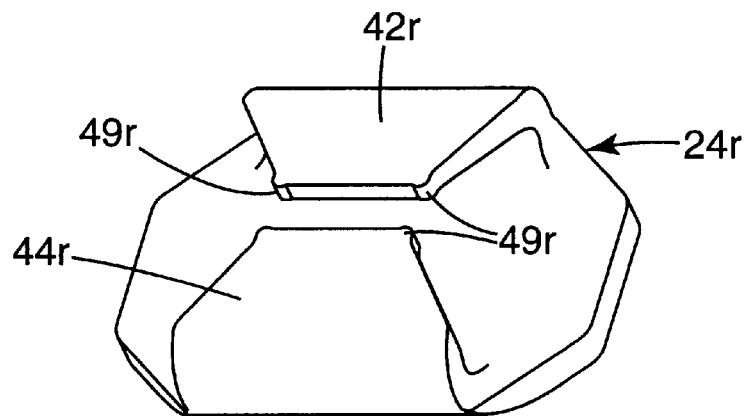
FIG. 36 is a perspective view of a carrier for an orthodontic bracket in accordance with still another embodiment of the invention.
Figure 37:
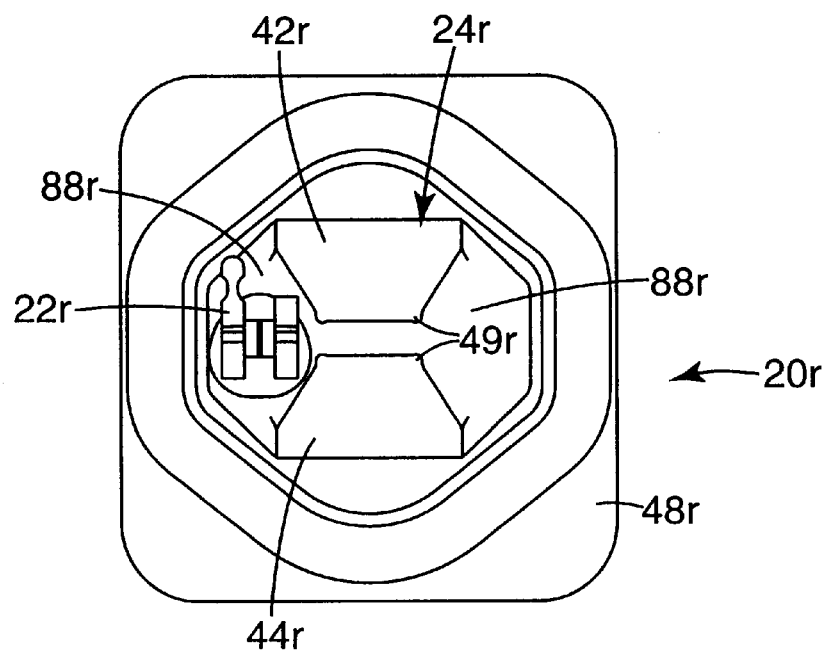
FIG. 37 is a plan view of an assembly that includes the carrier shown in FIG. 36 along with an orthodontic bracket and a container, wherein the bracket is shown as it appears immediately before it is lifted from the container by the practitioner.

An orthodontic assembly 20r that is constructed in accordance with another embodiment of the invention is illustrated in FIGS. 36 and 37, and includes a bracket 22r and a container 48r that are somewhat similar to the brackets and containers described above. Additionally, the assembly 20r has a carrier 24r (shown alone in FIG. 36) for releasably supporting the bracket 22r when received in the container 48r. The carrier 24r has a pair of arms 42r, 44r that extend toward each other and present a channel therebetween.

The arm 42r is received in a gingival recess of the bracket 22r, and the arm 44r is received in an occlusal recess of the bracket 22r. Preferably, the width of the outer end section of each arms 42r, 44r is somewhat greater than the distance between the mesial and distal sides of the bracket body, and each outer end section has a pair of outermost projections 49r. Preferably, each projection 49r extends for a small distance along either the mesial or distal sides of the bracket 20r in order to restrain lateral movement of the bracket 22r in directions along the length of the channel between the arms 42r, 44r. However, the projections 49r are sufficiently small and the arms 42r, 44r are sufficiently flexible so that the bracket 22r can be forcibly moved passed the projections 49r once grasped by a suitable tool and moved along the channel for removal from the container 48r.

The arms 42r, 44r and the container 48r are suitably constructed so that an opening 88r is presented adjacent at least one of the mesial and distal ends of the channel. The openings 88r are somewhat larger than the overall dimensions of the bracket 22r in plan view as shown in FIG. 37. Consequently, once the bracket 22r is moved by the practitioner along the channel, past the projections 49r and into one of the openings 88r, the bracket 22r can then be lifted from the container 48r for use as needed.

The carrier 24r may be constructed of material similar to the materials of construction of the carriers described above. Optionally, the arms 42r, 44r are sufficiently flexible to enable removal of the bracket 24r by sliding the bracket 22r to the opening 88r, or alternatively by simply lifting the bracket 22r and forcibly spreading the arms 42r, 44r due to such lifting movement. The overall size of the container 48r may be somewhat reduced from that shown in FIGS. 36–37 by eliminating one of the openings 88r such that one side of each arm 42r, 44r is in close proximity to the adjacent sidewall section of the container 48r.

As an option, the arms 42r, 44r may include an elongated ridge that extends along an upper, outer corner edge of their respective outer end sections. The ridges are sized to matingly fit within semi-cylindrical grooves extending beneath the tiewings of the bracket 22r, in order to help prevent the bracket 22r from twisting about its labial-lingual axis. Such ridges are particularly useful for single wing brackets due to the relatively short overall width of the tiewings. An adhesive, a roughened surface or other structure may be provided in place of or in addition to the ridges to either help prevent against sliding motion of the bracket 22r along the channel between the arms or to help prevent against unintentional twisting motion of the bracket 22r.

Optionally, the shape of the channel between the arms 42r, 44r may be such that turning the bracket 22r ninety degrees about its labial-lingual axis enables the bracket 22r to be lifted from the container 48r without significant opening movement of the arms 42r, 44r. In that instance, the arms 42r, 44r could be less flexible or even substantially rigid. For example, in instances where the bracket 22r has an overall rectangular shape with an overall occlusal-gingival dimension beneath the tiewings that is greater than the overall mesial-distal dimension in the same plane, turning the bracket 22r about its labial-lingual axis in the channel causes the arms 42r, 44r to disengage the bracket recesses and enable the bracket 22r to be lifted from the container 48r without further movement of the arms 42r, 44r (assuming the base of the bracket 22r is also clear of contact with the arms 42r, 44r). Such construction avoids the need for the openings 88r and is particularly useful for single tiewing brackets. The arms 42r, 44r are preferably provided with ridges, adhesives, roughened surfaces and/or other structure as mentioned above when used with this option to help prevent unintentional rotational movement of the bracket 22r.

Figure 38:
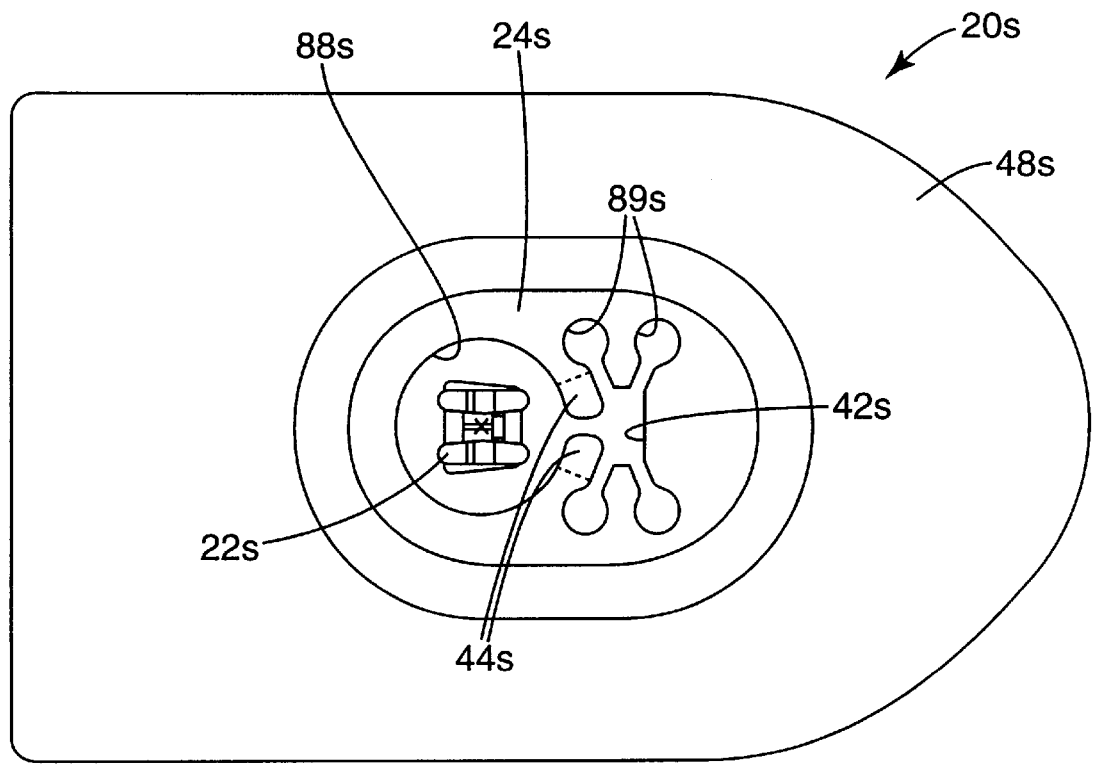
FIG. 38 is a plan view of an orthodontic assembly that includes a bracket, a carrier and a container according to an additional embodiment of the invention.
Figure 39:
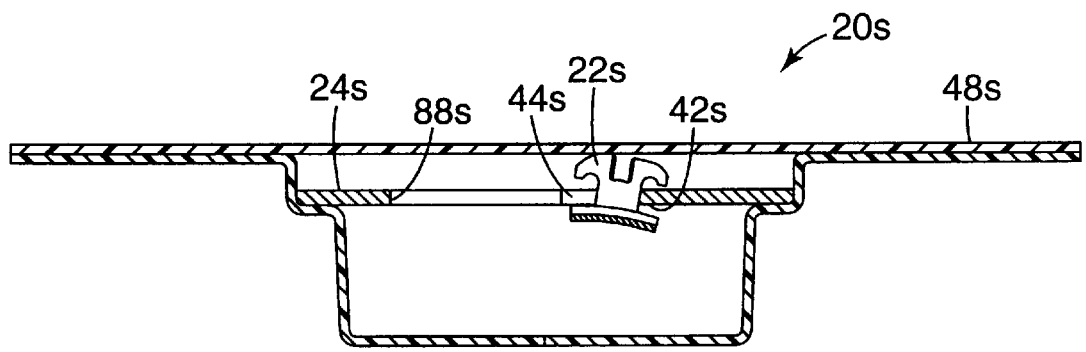
FIG. 39 is a side cross-sectional view of the assembly shown in FIG. 38.

An orthodontic assembly 20s according to the embodiment of the invention that is illustrated in FIGS. 38 and 39 also includes a bracket 22s and a container 48s. Preferably, the bracket 22s and the container 48s are the same as or similar to the brackets and containers described earlier. The bracket 22s is removed from the container 48s by sliding the bracket 22s in a lateral direction to an opening 88s before lifting the bracket 22s from the container 48s. The bracket 22s is shown in its location supported by the carrier 24s in FIG. 39, while in FIG. 40 the bracket 22s is shown as it appears once moved to the opening 88s.

In FIGS. 38 and 39, the bracket 22s is supported by a carrier 24s that preferably is secured to a shoulder formed on a side wall of the container 48s. Alternatively, however, the carrier 24s could be integrally molded with the container 48s to form a unitary, one piece construction.

The carrier 24s includes an arm 42s that is received in a gingival or occlusal recess of the bracket 22s. The carrier 24s also includes a pair of spaced-apart arm sections 44s that are received in the other of the occlusal and gingival recess of the bracket 22s. Preferably, the space between the arm sections 44s is sufficiently small to prevent unintentional lateral movement of the bracket 22s into the opening 88s, and yet sufficiently large to enable the bracket 22s to be forcibly moved passed the arm sections 44s and into the opening 88s for subsequent lifting and removal of the bracket 22s from the container 48s when desired. The carrier 24s includes four keyhole-shaped relief areas 89s that facilitate deflection and movement of adjacent sections of the carrier 24s (and particularly deflection of the arm sections 44s) as the bracket 22s is moved toward the opening 88s.

In each of the embodiments described above, the outer ends of the arm sections supporting the brackets optionally may extend at an angle other than 90 degrees relative to the direction of extension of the arms toward the bracket, in order to accommodate brackets having bodies having corresponding shapes. Similarly, the outer ends of the supports described above may extend at an angle to mate with the mesial and distal sides of the supported bracket.

Figure 40:
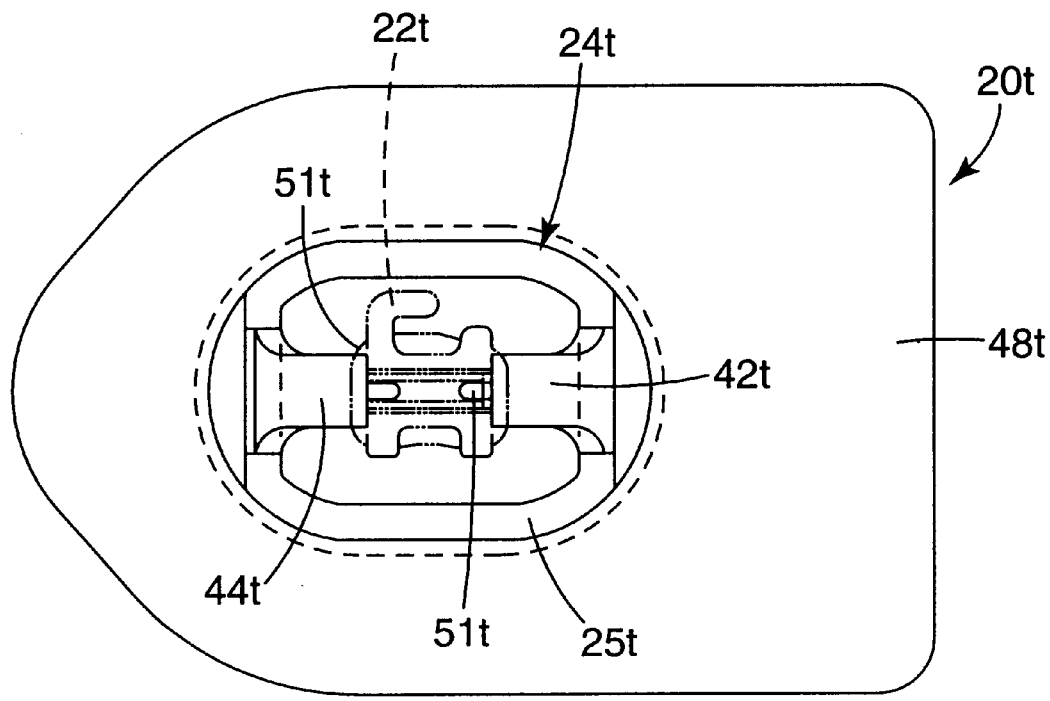
FIG. 40 is a plan view of an orthodontic assembly according to yet another embodiment of the invention, wherein the assembly includes an orthodontic buccal tube, a carrier and a container.

An orthodontic assembly 20t according to another embodiment of the invention is illustrated in FIG. 40 and includes an orthodontic bracket appliance that in this instance is a buccal tube 22t (shown in phantom lines). (As used herein, a buccal tube is a bracket). The assembly 20t also includes a carrier 24t for releasably supporting the buccal tube 22t within a container 48t. Although not shown, the buccal tube 22t preferably contains a layer of orthodontic adhesive that is coated onto a base of the buccal tube 22t.

The carrier 24t is somewhat similar to the carrier 22i described above, in that the carrier 24t has a bottom section 25t with a somewhat ring-shaped configuration, and also includes a pair of arms 42t, 44t that extend upwardly from the bottom section 25t. Furthermore, the carrier 24t is preferably initially flat and includes a living hinge between the bottom section 25t and each of the arms 42t, 44t. However, unlike the carrier 22i, each of the arms 42t, 44t includes a pin-shaped outer end section 51t. One of the pin-shaped outer end sections 51t is located in a mesial recess of the buccal tube 22t while the other of the pin-shaped outer end sections 51t is received in a distal recess of the buccal tube 22t.

Preferably, the aforementioned mesial recess and distal recess of the buccal tube 22t are part of a common passage that extends through the buccal tube 22t in a mesial-distal direction. For example, the passage containing the mesial and distal recesses could be a passage for ultimately receiving the archwire when the buccal tube 22t is in use during the course of orthodontic treatment. Alternatively, the mesial and distal recesses could be part of other passages of the buccal tube 22t, such as a passage for a headgear wire section or for an auxiliary wire section.

In use, the carrier 24t functions in a manner similar to the carrier 24i, in that the arms 42t, 44t self-move in an arc away from each other and spread apart from the buccal tube 22t as the latter is lifted from the container 48t. Such swinging movement of the arms 42t, 44t is facilitated by provision of living hinges as described above, or alternatively by lines of weakness or other structure at the location where the arms 42t, 44t connect with the bottom section 25t. Alternatively, the arms 42t, 44t may be directly connected by adhesive, tack welding or other suitable means to the side walls or the base of the container 48t, or optionally integrally connected with the side walls or the base of the container 48t.

Figure 41:
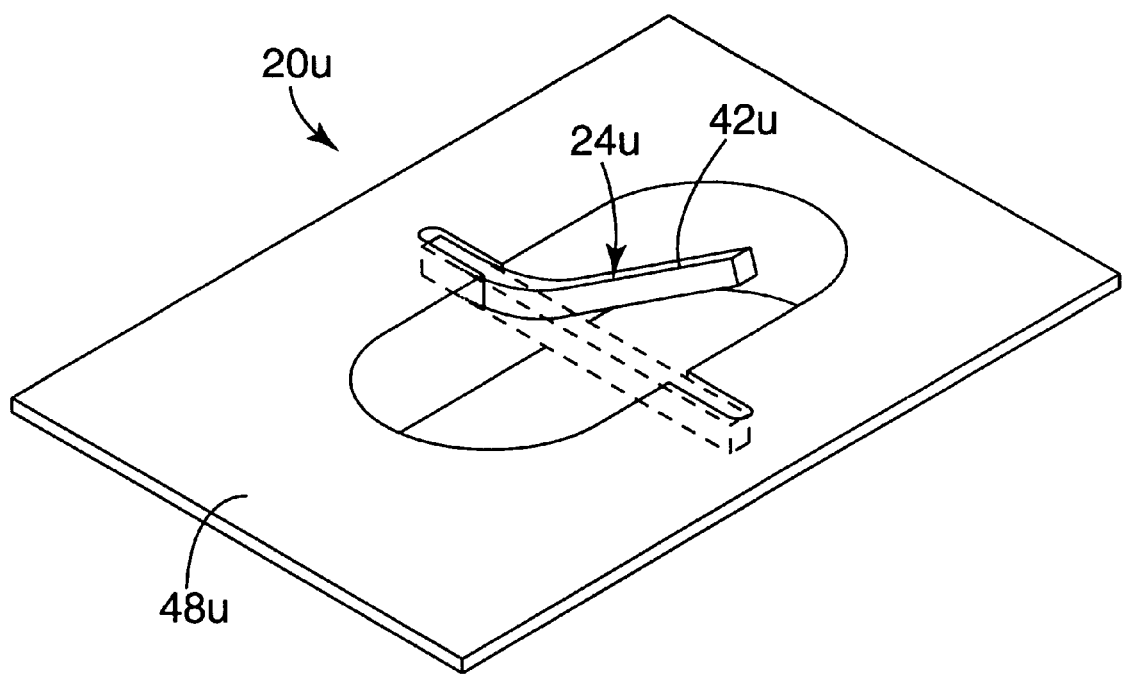
FIG. 41 is a perspective view of an orthodontic assembly constructed in accordance with another embodiment of the invention.

An orthodontic assembly 20u according to another embodiment of the invention is illustrated in FIG. 41 and includes a buccal tube (not shown), a carrier 24u and a container 48u. The carrier 24u includes an arm 42u that is fixed on one end to a cavity formed in an adjacent interior sidewall section of the container 48u. The arm 42u has a rod-like or wire-like configuration adapted to fit into a passage of the buccal tube. In FIG. 41, the arm 42u is received in an archwire slot of the buccal tube, although alternatively the arm 42u could be received in other recesses such as a passage for a headgear wire section or an auxiliary wire section. The arm 42u is preferably made of a metallic wire material or a plastic material molded to present a wire-like shape.

The arm 42u extends at least partially along the length of the archwire slot, and preferably extends along the entire length of the archwire slot. The outer end of the arm 42u is received in a cavity on an opposite sidewall section of the container 48u. As the buccal tube is lifted from the container 48u, the outer end of the arm 42u is pulled from the adjacent cavity, and the arm 42u also slides out of the archwire slot and ultimately disengages from the buccal tube.

Although not shown in FIG. 41, a cover preferably extends over the container 48u. As an option, the cavities receiving the buccal tube are located at a depth from the top of the container 48u that is sufficient to enable the arm 42u to support the buccal tube below the top of the container 48u. In this manner, the cover is not bulged in areas over the buccal tube.

As another option, two aligned arms could be provided in the container 48u, with each arm extending from an opposite sidewall of the container 48u. In such a construction, adjacent outer ends of the arms may be temporarily joined together or integrally molded together with sufficient weakness that the arms readily separate from each other as the buccal tube is lifted from the container 48u. The arms slide out of respective ends of the archwire slot during removal of the buccal tube from the container 48u. The archwire slot, or other passage receiving the arm or arms, is considered for present purposes as providing a recess or recesses for receiving the arm or arms.

Figure 42:
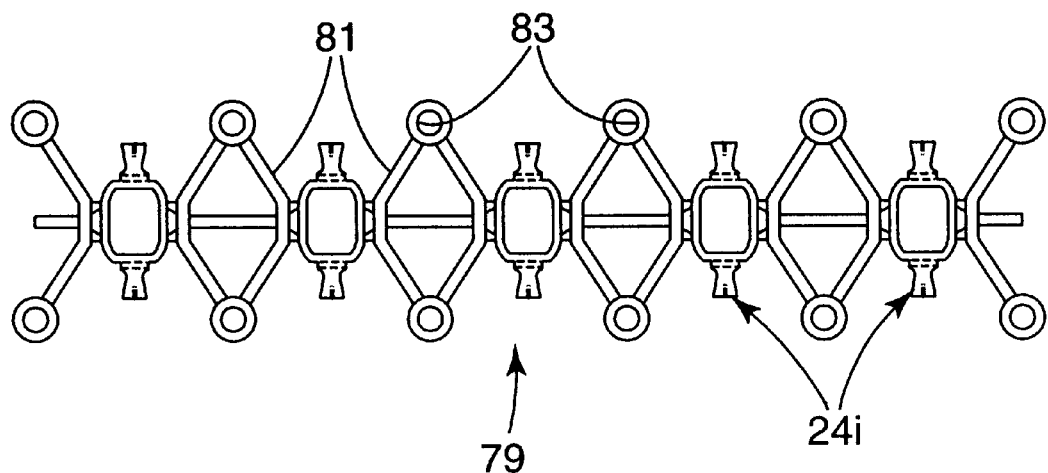
FIG. 42 is a plan view of a chain segment useful during manufacture of carriers.

FIG. 42 is an illustration of a chain segment 79 that is useful as an intermediate molded structure when manufacturing some of the carriers described above. For exemplary purposes, the chain segment 79 includes a number of the carriers 24i of the type shown in FIGS. 16–17, although carriers according to other embodiments of the invention alternatively could be provided. The carriers 24i are illustrated as they appear after molding and before the arms are folded upwardly for insertion into a container. Each carrier 24i is connected to adjacent carriers 24i by an indexing member 81 having a pair of opposed, outboard apertures 83.

The chain segment 79 is preferably molded as a continuous member, optionally by advancing the member a distance equal to a number of carriers 24i and then molding a number of additional carriers 24i and indexing members 81 on the trailing end of the previously-molded segment 79. The apertures 83 provide a location for a sprocket wheel or other device to move the chain segment 79 in automated, timed fashion when desired. If desired, automated movable assembly equipment may be provided to close the arms against the brackets and then place the carriers 24i into containers once the indexing members are detached.

Figure 43:
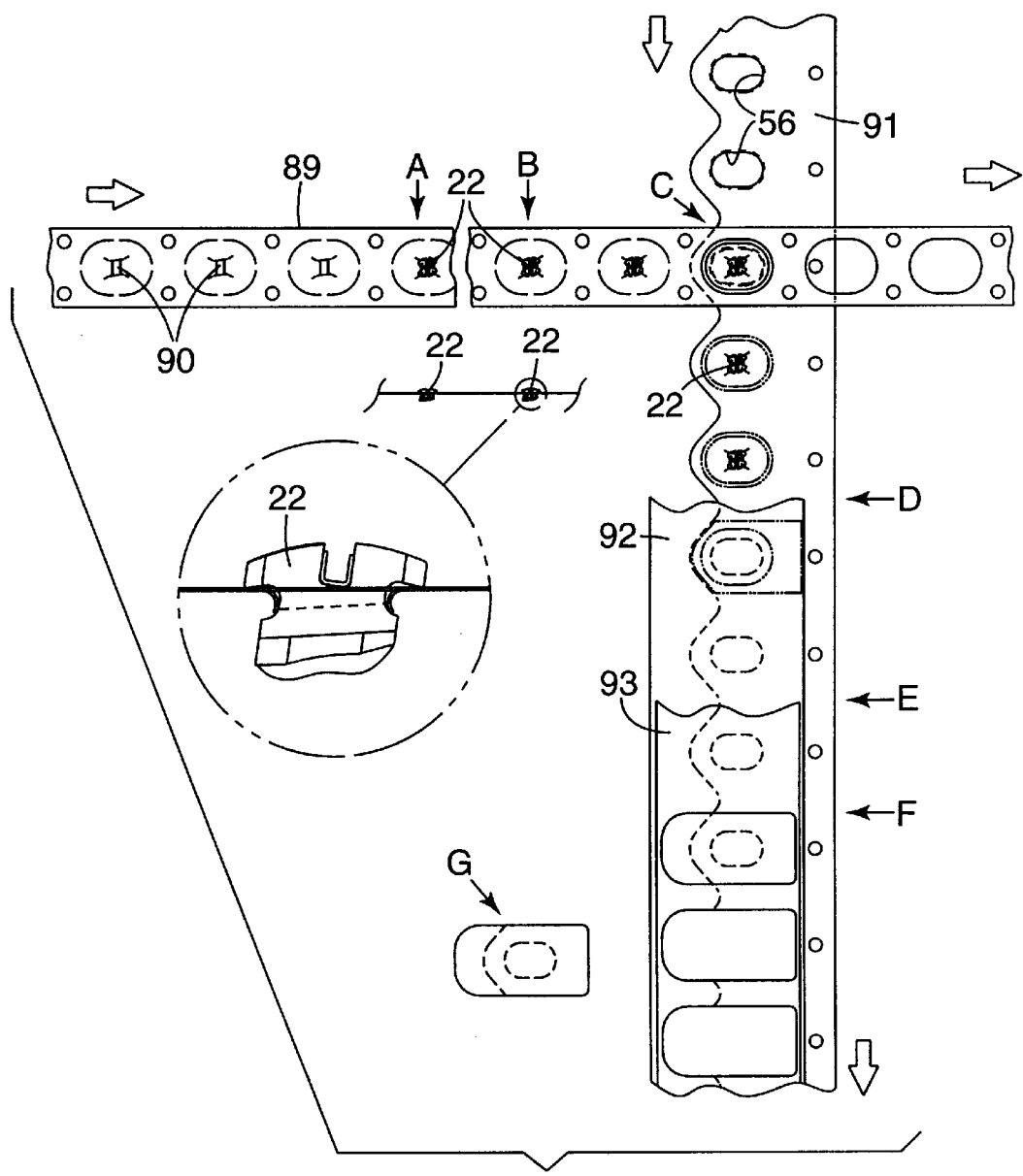
FIG. 43 is a fragmentary, reduced plan view in partially schematic form showing one method for placing orthodontic brackets in containers in automated fashion to manufacture the assemblies depicted in some of the embodiments of the previous illustrations.

FIG. 43 is a schematic illustration of an automated method of manufacture that is useful for making some of the assemblies described above, and in particular is useful for making assemblies wherein the carrier has a somewhat flat configuration at least in areas adjacent the bracket. In FIG. 43, a web 89 has a series of openings 90 and moves in the direction of the arrow. Each of the openings 90 has tear lines radiating from its corners in order to present flexible arms and/or supports similar to the arms and/or supports described above for releasably supporting and engaging brackets 22. Preferably, the web 89 is die cut from a strip of stiff plastic sheet material such as polyester, acetate, polypropylene, polyethylene, cellulose plastics and the like. The web 89 also includes a series of holes extending along both sides to receive a sprocket drive wheel or other device for advancing the web 89.

The arms and/or the supports surrounding the openings 90 are sufficiently flexible or otherwise moveable to enable the brackets 22 to be placed into the openings 90 as well as removed from the openings 90 when desired. In the method of manufacture shown in FIG. 43, the brackets 22 are placed into the openings 90 at the location marked "A", preferably by an automated placement tool such as a robot arm. As an example, the brackets 22 may be placed into the openings 90 by rocking the brackets 22 in a manner similar to rocking motion of a button when placed into a buttonhole.

Next, a layer of orthodontic adhesive is applied to the base of each bracket 22 at the location marked "B". As an alternative, the adhesive could be applied to each bracket 22 before the brackets 22 are placed into the openings 90 of the web 89. The web 89 then advances as necessary to sequentially bring each bracket 22 to the location designated "C".

A strip 91 of material is formed with a series of wells 56 as well as another series of holes to receive a sprocket drive wheel or other advancement device. As each well 56 approaches the location "C", the well 56 comes into registration with one of the openings 90 and the associated bracket 22. Next, advancement of the strip 91 and the web 89 is halted and a die, a knife or other suitable separation means is lowered to separate a carrier section of the web 89 surrounding each bracket from remaining sections of the web 89, preferably without cutting the strip 91. The carrier sections shown in FIG. 43 have a somewhat oval-shaped configuration, although other configurations are also possible.

Preferably, the carrier sections are substantially precut, partially removed or at least weakened from adjacent portions of the web 89 before reaching the location marked "C", so that the carrier sections are only weakly connected to remaining portions of the web 89 and can be easily removed. For example, the carrier sections could be precut in advance except for a few small tabs that remain to hold the sections in place before reaching the location marked "C". As a consequence, the carrier sections may be easily separated from remaining portions of the web 89 by a movable platen, die or the like without cutting or otherwise damaging the strip 91 in areas surrounding the underlying well 56. Preferably, the movable platen has a heated lower end that serves to weld or heat-seal the carrier section to the strip 91, although an adhesive could also be used to connect the detached carrier section to the strip 91.

Next, the strip 91 is advanced along the direction along the arrow shown in FIG. 43, and a roll 92 of lidding material is lowered into contact with the strip 91 at the location marked "D". At the location "D", the roll 92 of lidding material is also preferably secured to the strip 91 adjacent the periphery of each well 56 by a pressure sensitive adhesive, by a heated platen or other suitable means. The strip 91 along with the roll 92 are then advanced simultaneously in the direction of the arrow shown in FIG. 43 to the location designated "E".

At the location "E", a roll 93 of label stock is brought down into contact with the upper face of the roll 92 and is preferably secured to the latter by a pressure sensitive adhesive or other suitable means. Next, the strip 91, the roll 92 and the roll 93 are advanced to the location designated "F", where a knife or other cutting device is lowered to cut the strip 91 as well as both of the rolls 92, 93 along lines that represents the desired shape of the lid or cover. The finished container (shown at "G") is then removed from remaining sections of the strip 91 and the rolls 92, 93. In the finished container according to the illustrated embodiment, the cover bulges in areas over the bracket since the labial face of the tiewings extends above the well 56. However, the web 89 could be modified to present recesses or wells that are shaped to fit within the wells 56 if desired, so that the cover of the finished container extends flatly across the labial face of the tiewings as well as across the well 56.

Figure 44:
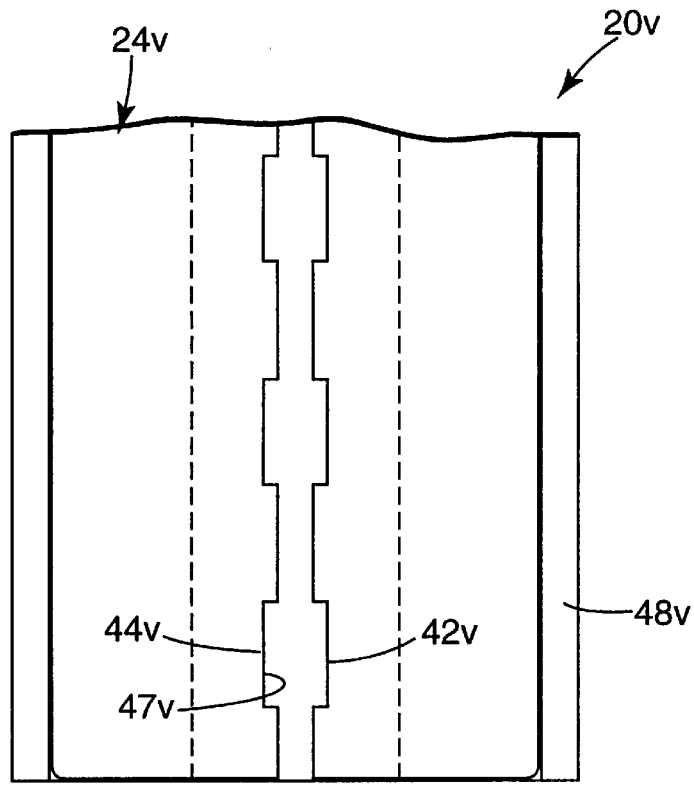
FIG. 44 is a plan view of another orthodontic assembly according to the invention except that brackets of the assembly have been omitted.
Figure 45:
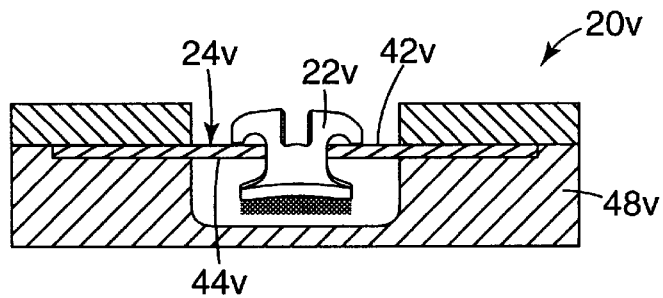
FIG. 45 is a side cross-sectional view of the assembly shown in FIG. 44.

An orthodontic assembly 20v according to another embodiment of the invention is shown in FIGS. 44–45 and includes a bracket 22v (shown only in FIG. 45), a carrier 24v and a container 48v. The carrier 24v includes two separate, spaced apart sections and has a flat configuration with a series of rectangular notches 47v similar to the notches 47c described above. Flexible arms 42v, 44v are located adjacent each notch 47v and releasably fit into gingival and occlusal recesses of the bracket 22v. Optionally, lines of weakness such as perforations, tear lines and the like extend outwardly from corners of each notch 47v to facilitate movement of the arms 42v, 44v during removal of the bracket 22v from the container 48v.

The carrier 24v is preferably made of a plastic or boxboard material, and the container 48v is preferably made of a rigid plastic or foam material. As shown in FIG. 45, the container 48v includes a lower section and an upper section that is joined to the lower section after the carrier 24v is placed between the upper and lower sections. In FIG. 44, the upper section is omitted. A cover (not shown) extends over the top of the upper section.

The assembly 20v is particularly suitable in an automated manufacturing operation, since the carrier 24v initially may be part of a continuous, coiled strip of material that is advanced to a location where brackets 22v are placed into the notches 47v. The carrier 24v can then be used to support the brackets 22v as the brackets 22v are moved to another processing location, such as a location where an orthodontic adhesive is applied to the base of each bracket 22v. Subsequently, the brackets 22v are advanced to a location where upper and lower sections of the container 48v are brought into contact with the carrier 24v and joined together, and where lidding material is applied. The container 48v and the carrier 24v can then be cut to any suitable length (such as a length containing 1 to 5 brackets) to provide a package for shipment to the practitioner.

Figure 46:
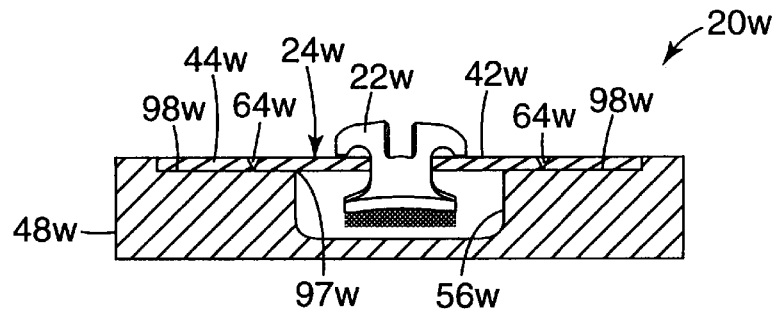
FIG. 46 is a side cross-sectional view of an orthodontic assembly according to another embodiment of the invention.

An orthodontic assembly 20w constructed according to another embodiment of the invention is shown in FIG. 46 and includes a bracket 22w, a carrier 24w and a container 48w. The carrier 24w includes two sections that are optionally separate from one another. One section includes a flexible arm 42w that fits with a gingival recess of the bracket 22w, and the other section includes a flexible arm 44w that fits within an occlusal recess of the bracket 22w.

The container 48w includes well 56w and a shoulder portion 97w located on opposite sides of the well. Each shoulder portion 97w is located between the bracket 22w and a line of weakness 64w of each arm 42w, 44w. Each of the arms 42w, 44w is connected to the container 48w at a location outwardly (relative to the bracket 22w) from the line of weakness 64w, such as the location designated 98w in FIG. 46. The arms 42w, 44w may be connected to the container 48w by an adhesive (including a double-sided adhesive tape), welding or any other suitable means.

When the bracket 22w is lifted from the well 56w, the arms 42w, 44w are easily raised in an opening motion due to the lines of weakness 64 and due to the outwardly locations of the connections 98w. However, the shoulders 97w, being located inwardly (relative to the bracket 22w) from the lines of weakness 64, help resist movement of the arms 42w, 44w in a downwardly direction. As a consequence, it takes less force to bend the arms 42w, 44w in an upwardly direction than in a downwardly direction (viewing FIG. 46) and the probability of contact of the bottom of the well 56w with adhesive on the base of the bracket 22w is reduced.

Preferably, the well 56w has an oval-shaped configuration adapted to support a single bracket 22w, although other configurations are also possible. A cover (not shown) extends over the top of the bracket 22w in bulged fashion and is releasably connected to the container 48w. Optionally, the arms 42w, 44w are received in a deeper cavity of the container 48w than that shown in FIG. 46, so that the cover extends flatly across the top of the container 48w.

Figure 47:
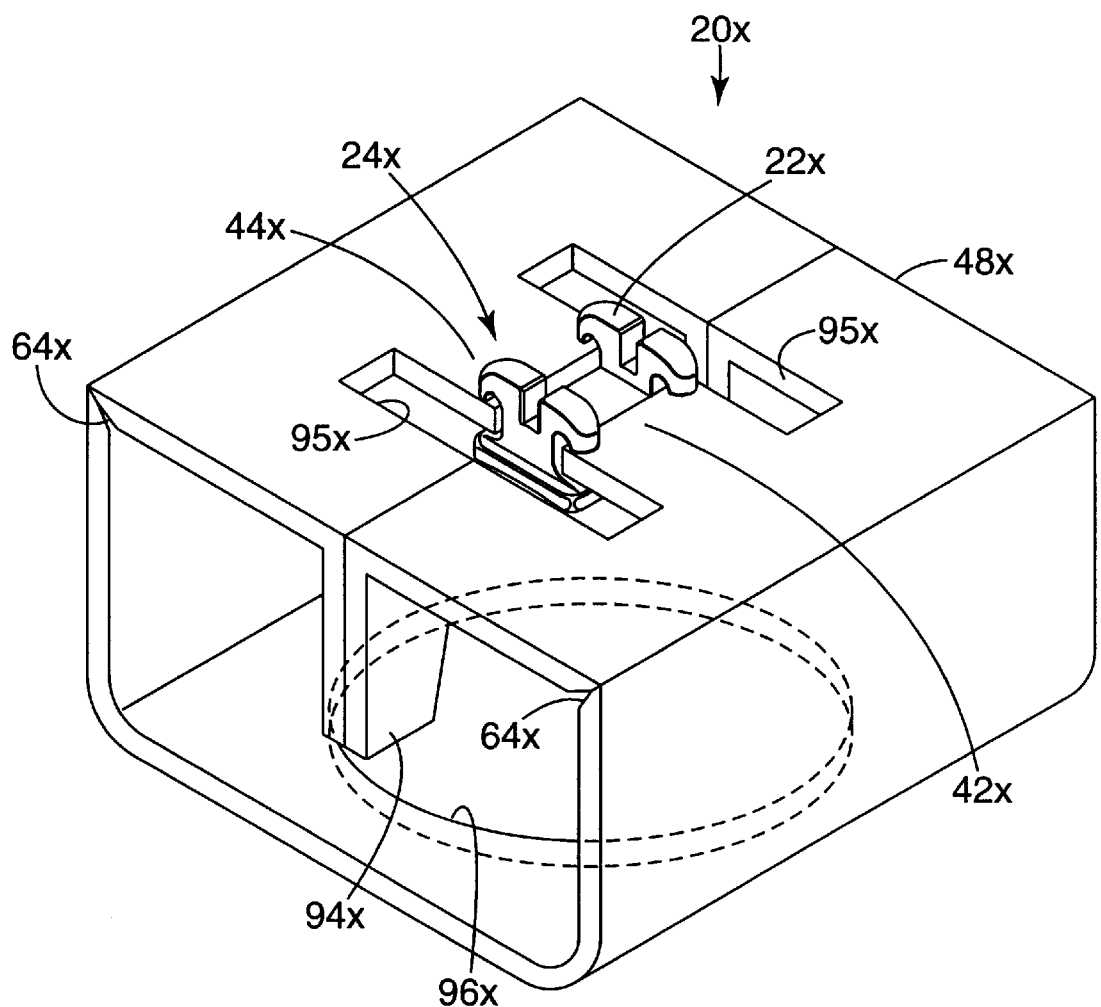
FIG. 47 is a perspective view of an orthodontic assembly according to another embodiment of the invention.

An orthodontic assembly 20x according to another embodiment is depicted in FIG. 47 and includes a bracket 22x, a carrier 24x and a container 48x. In this instance, the container 48x is integral with the carrier 24x. The carrier 24x has opposed arms 42x, 44x that fit within gingival and occlusal recesses of the bracket 22x.

The container 48x has a rectangular shape in cross-sectional view, and may be made by extrusion or by folding a length of flat stock. Optionally, the container 48x is elongated and supports a number of brackets 22x. Preferably, the container 48x includes depending struts 94x that increase the rigidity and rack resistance of the container 48x. The struts 94x preferably have sufficient length to contact the bottom of the container 48x, although such contact is not shown in FIG. 47.

Optionally, the depth of the struts 94x and the sidewalls of the container 48x can be varied to accommodate for the labial-lingual dimension of different brackets.

The container 48x includes two slots 95x of a size adapted to receive legs of dental tweezers. The slots 95x enable the practitioner to securely grasp the mesial and distal sides of the bracket 22x during removal of the latter from the container 48x. In certain of the embodiments described above, similar slots could be provided in the containers or alternatively in the carriers.

The container 48x includes lines of weakness 64x extending along the outer edges of the top wall sections and the upper edges of the side wall sections of the container 48x. As the bracket 22x is lifted from the carrier 24x, the top wall sections pivot relative to the sidewall sections and open outwardly such that the arms 42x, 44x disengage the gingival and mesial recesses of the bracket 22x. As an alternative, however, living hinges or other hinge structure could be provided between the arms 42x, 44x and respective portions of the container top wall sections, such that the top wall sections remain stationary while the arms 42x, 44x pivot upwardly and outwardly. In that alternative, the struts 94x may be joined together by an adhesive, by welding or other suitable means.

The assembly also is useful in an automated manufacturing operation, as the container 48x and the carrier 24x can be provided as a continuous strip of material that supports a number of brackets 22x. Preferably, a bottom wall of the container 48x has an opening 96x below the area where each bracket 22x is received. The openings 96x enable the brackets 22x to be placed into the carrier 24x in automated fashion and in a labial direction of the brackets 22x such that the curved tiewings of the brackets 22x serve to bend and spread apart the arms 42x, 44x during placement into the carrier 24x. The openings 96x also provide for convenient access to the base of the brackets 22x during a subsequent manufacturing operation, such as during a process of applying orthodontic adhesive to the base of each bracket 22x.

The container 48x may be cut to any suitable length as desired, such as a length containing 1 to 5 brackets. Optionally, a cover (not shown) extends over the top section of the container 48x in bulged fashion, and also extends over ends and openings 96x to protect the brackets 22x and any adhesive from contaminants, and to prevent any adhesive from undue curing. As another option, the container 48x is placed into a well of a separate package having a cover.

In each of the embodiments set out above, the carriers, brackets and containers (including the covers) may have features or be made of materials described in connection other embodiments. Moreover, a variety of modifications to the various embodiments may be apparent to those skilled in the art without departing from the spirit of the invention. Accordingly, the invention should not be limited to the currently preferred embodiments that are described in detail above, but only by a fair reading of the claims that follow along with their equivalents.

We claim:

1. An assembly including:
   an orthodontic bracket having a base, a body extending from said base and at least two opposed tiewings extending away from said body, said base and at least one of said tiewings extending past said body in a gingival direction and presenting a gingival recess, said base and at least one other of said tiewings extending past said body in an occlusal direction and presenting an occlusal recess; and
   a carrier having a pair of arms extending toward each other, each of said arms having an outer end section, said outer end sections being spaced apart from each other and presenting a channel therebetween, said bracket being located in said channel and being supported by said arms with one of said outer end sections extending into said occlusal recess and the other of said outer end sections extending into said gingival recess.

2. The assembly of claim 1 wherein said arms are flexible.

3. The assembly of claim 1 wherein said arms are movable away from each other to enable release of said bracket.

4. The assembly of claim 3 wherein said arms are flexible and include lines of weakness to facilitate movement away from each other.

5. The assembly of claim 3 wherein said arms are flexible and moved past their yield point when moved away from each other during release of said bracket.

6. The assembly of claim 1 wherein said bracket includes a mesial side and a distal side, and wherein said carrier also includes a pair of supports extending toward each other, one of said supports having an outer end portion adjacent said mesial side and the other of said supports having an outer end portion adjacent said distal side.

7. The assembly of claim 1 wherein said carrier is made of a folded, unitary section of material.

8. The assembly of claim 1 and including an adhesive extending across said base of said bracket.

9. The assembly of claim 1 and including a container having a substrate and a well that receives said carrier and said bracket, said container including a cover extending across said well and in contact with said bracket.

10. The assembly of claim 9 wherein said container is integrally connected to said carrier.

11. The assembly of claim 9 wherein said container is adhesively joined to said carrier.

12. The assembly of claim 9 wherein said container is joined to said carrier by a heat seal or weld.

13. The assembly of claim 9 wherein said cover has a shape that matches the shape of at least a portion of said tiewings including curved portions of said tiewings.

14. The assembly of claim 9 wherein said arms are flexible and wherein said cover presses against said bracket with sufficient force to deflect said arms in a direction away from said cover.

15. The assembly of claim 9 and including a hermetic seal between said cover and said substrate.

16. The assembly of claim 9 and including a repositionable adhesive between said cover and said substrate.

17. The assembly of claim 9 wherein one of said substrate and said carrier includes a key and wherein the other of said substrate and said carrier includes a keyway that matingly receives said key.

18. The assembly of claim 17 wherein said keyway receives said key in snap-fit relation.

19. The assembly of claim 17 wherein said keyway comprises a hole located in said carrier at a position remote from said bracket.

20. The assembly of claim 9 including an opening adjacent said channel of sufficient size to enable removal of said bracket from said container once said bracket has been moved along said channel to said opening.

21. The assembly of claim 20 wherein at least one of said arms includes a projection adjacent said opening for substantially precluding unintentional movement of said bracket along said channel and to said opening.

22. The assembly of claim 1 wherein said carrier has a ring-shaped bottom section.

23. The assembly of claim 1 wherein said base of said bracket faces away from said carrier.

24. The assembly of claim 1 wherein said tiewings of said bracket face away from said carrier.

25. The assembly of claim 1 wherein said channel, said occlusal recess and said gingival recess have approximately equal lengths.

26. The assembly of claim 1 wherein said carrier has a flat bottom section remote from said channel.

27. An assembly comprising:
   an orthodontic buccal tube having a base, a body extending from the base, a mesial side and a distal side, said buccal tube including a mesial recess adjacent said mesial side and a distal recess adjacent said distal side; and
   a carrier having at least one arm extending into at least one of said recesses for supporting said buccal tube.

28. The assembly of claim 27 wherein said arm is flexible.

29. The assembly of claim 27 wherein two arms are provided, and wherein said arms are movable away from each other to enable release of said buccal tube.

30. The assembly of claim 27 and including an adhesive extending across said base of said buccal tube.

31. The assembly of claim 27 and including a container having a well that receives said carrier and said buccal tube, said container including a cover extending across said well and in contact with said buccal tube.

32. The assembly of claim 27 wherein said distal recess and said mesial recess are part of a passage that extends in a mesial-distal direction through said buccal tube.

33. A method of supporting orthodontic brackets comprising the steps of:
   providing a carrier having a pair of arms extending toward each other, wherein each arm includes an outer end section, and wherein the outer end sections are spaced apart from each other and present a channel therebetween; and
   moving a bracket along the channel until the bracket is located between the outer end sections, with one of the outer end sections received in an occlusal recess of the bracket and the other outer end section received in a gingival recess of the bracket.

34. The method as set out in claim 33, and including the step of providing a second carrier having a tubular member with a channel, and moving the second carrier relative to the brackets in order to position the brackets along the channel of the second carrier.

35. The method of claim 33 including the step of removing a bracket from the channel by sliding the bracket along the channel.

36. The method of claim 33 including the step of removing a bracket from the channel by spreading the arms a sufficient distance apart from each other to enable the bracket to disengage the carrier.

37. The method of claim 36 wherein said step of providing a carrier includes the step of folding a unitary section of material to present the arms extending toward each other.

38. The method of claim 33 including the step of applying an adhesive to a base of the bracket and the step of enclosing the arms and the bracket in a container.

* * * * *

UNITED STATES PATENT AND TRADEMARK OFFICE
CERTIFICATE OF CORRECTION

PATENT NO.: 6,089,861
DATED: July 18, 2000
INVENTOR(S): Kelly et al.

It is certified that error appears in the above-identified patent and that said Letters Patent is hereby corrected as shown below:

In col. 2, line 26, please insert ---to--- after "made".

In col. 2, line 48, please insert ---be--- after "otherwise".

In col. 3, line 36, please insert ---a--- after "is.

In col. 4, line 35 please insert ---in--- after "placed".

In col. 23, line 3, please insert ---with--- after "connection".

Signed and Sealed this

Eighth Day of May, 2001

Attest:

NICHOLAS P. GODICI

Attesting Officer

Acting Director of the United States Patent and Trademark Office